(12) United States Patent
Guo et al.

(10) Patent No.: US 6,593,110 B2
(45) Date of Patent: Jul. 15, 2003

(54) CHECKPOINT-ACTIVATING OLIGONUCLEOTIDES

(75) Inventors: Zijian Guo, San Diego, CA (US); William G. Dunphy, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/849,617

(22) Filed: May 4, 2001

(65) Prior Publication Data

US 2002/0086392 A1 Jul. 4, 2002

Related U.S. Application Data

(60) Provisional application No. 60/202,028, filed on May 4, 2000.

(51) Int. Cl.[7] .......................... C12P 21/06; C12N 1/20; C12N 15/00; C07H 21/04; C07K 17/00
(52) U.S. Cl. ................ 435/69.1; 435/252.3; 435/320.1; 536/23.5; 530/352
(58) Field of Search .................. 536/23.2, 23.5; 435/810, 320.1, 252.3, 69.1; 530/352

(56) References Cited

U.S. PATENT DOCUMENTS 5,073,486 A * 12/1991 Leonard et al.
5,532,347 A * 7/1996 Cone et al.
5,738,844 A * 4/1998 Beckmann et al.
6,048,693 A 4/2000 Bitter

OTHER PUBLICATIONS

Sambrook, J., Fritsch, EF, and Maniatis, T., in Molecular Cloning: A Laboratory Manual. Cold Spring Harbor Laboratory Press, NY, vol. 2 (1989), p. 11.7.*
Bargues, et al., "Direct Submission," Apr. 2000, pp. 1–39, (Genbank) NCBI [on–line]. Accession No. AL133363.
Furnari et al., "Cdc25 Inhibited In Vivo and In Vitro by Checkpoint Kinases Cds1 and Chk1," *Molecular Biology of the Cell*, Apr. 1999, vol. 10, pp. 833–845.
Guo et al., "Response of Xenopus Cds1 in Cell–free Extracts to DNA Templates with Double–stranded Ends," *Molecular Biology of the Cell*, May 2000, vol. 11, 1535–1546.
Sugano et al., "Wash. U. Zebrafish EST Project 1999". Jun. 1999, pp. 1–2, (Genbank) NCBI [on–line]. Accession No. AI667584.

* cited by examiner

*Primary Examiner*—Christina Chan
*Assistant Examiner*—Maher Haddad
(74) *Attorney, Agent, or Firm*—Gray Cary Ware & Freidenrich, LLP

(57) ABSTRACT

The present invention provides polypeptides (Cds1) that are involved in regulating the progression of the cell cycle. The polypeptides are activated by double-stranded DNA and phosphorylated in response to the presence of double-stranded DNA. Also provided are polynucleotides encoding Cds1 polypeptidese and methods for modulating cell cycle progression in a cell.

8 Claims, 5 Drawing Sheets

FIGURE 1

```
ctgagatttt acttgaaatg aaggcgaggg cctgataggt tatgatttgc aaagagcgtg   61
ggttcaggat catttgtctg tactgtaaag tgttattagc gctaatattt cgcttcaggt  121
aaaagagggg cgtgcgccac aggtgctgga gacggggagc gcctttccgc tgctggagaa  181
acgcacgcac attcacctgc agcaaaacaa gctttccagg taaatgatgt ctcgtgatac  241
taaaacagag tcgcaacaat ctcagggcac ttcaagttcc tcgtcctcca gtgctcctca  301
atcttacagt cagtcgtctt catcgggtac attaagttct tggatactg ttccagtgca  361
agatcttgcg tccattcctg aagaccctga gatagacgag gatataccc agccttgggg  421
tcgtctctgg gctcttggga agggctttct aaatcatgat tgcctgcatg aagaatatgt  481
atttggaaga gacaaaaaat gtgattacac ctttgatatt ccagtactaa accagaccga  541
caggtacaaa acatatagca aaaggcactt cagaatattt caggaattag gtcatggaca  601
ctcccgtgtt gctaacatag aagatctgag cggcaacgga catttgtta acaaggagat  661
tattggaaaa gggcggacat tgcctttaac aaataatgcc gagattgcac tttcattacc  721
aactaataaa gttttgtttt tttcagattt gtctgtggat gatcagacta tatatcctaa  781
ggacttcatt gataaataca tcatgtcaag gccaatcgga agtggggctt gcggggaagt  841
gaaattggct tttcaaaagt cagtatgcaa gaaggttgct gtaaaaatca tcagtaaaag  901
aaaatttaaa atgaacactt ctagtaatga cacccctata tctgttgaca cagaaataga  961
gatcctgaaa aaacttgatc atccctgtat cattaaaata gagaattttt ttgactctga 1021
ggacttctat tacattgtgt tggaactgat ggaaggaggc gaactgtttg acagggtggt 1081
aaattcgaca agactccgag aaccaattgc caaactgtat ttttatcaga tgctgctagc 1141
tgttcagtac ctccatgaaa atggggtgat acatcgtgat ctgaagcctg aaaatgtgct 1201
gttgtcatcc actagtgaag aatgttgcat aaagataacg gattttggac agtcaaaaat 1261
tctgggtgaa acgtctttaa tgagaacttt gtgtggaact cctacatact ggcgcctga 1321
agttttgaat acagcaggca caactggata cagtagtgca gtggattgct ggagtttagg 1381
agtcatcctt tttgtgtgtc tttgtggata tcccccctt tcagaacaaa atagtaacat 1441
tcccttgaaa aatcagattg cagagggaaa atacacctac attgctgctg cttggagaaa 1501
tgtatcagaa caagcatttg atttagtcaa gaatcttctt gttgttgatc ctgagcaaag 1561
acttaccact aaacaagcac tggaacatcc ctggcttcag gacgattcta tgaagcatac 1621
tgttgaaagg ttaatgtatg gggttgacca cacaatgcct cctccaatca agaaaaacat 1681
aattcgaaaa cggggacatg aatgggatca agatgccagt acttcatctt gctcagagat 1741
attaccaaca tcagccgaaa agagagcaaa aagataaaac aaaaaaaata cattgcgctt 1801
tatttaataa atgttttgt aaaaaaaaaa aaaaaaaaa aaaaa
```

FIGURE 2

```
MMSRDTKTES QQSQGTSSSS SSSAPQSYSQ SSSSGTLSSL DTVPVQDLAS IPEDPEIEDED   61
IPQPWGRLWA LGKGFLNHDC LHEEYVFGRD KKCDYTFDIP VLNQTDRYKT YSKRHFRIFQ  121
ELGHGHSRVA NIEDLSGNGT FVNKEIIGKG RTLPLTNNAE IALSLPTNKV FVFSDLSVDD  181
QTIYPKDFID KYIMSRPIGS GACGEVKLAF QKSVCKKVAV KIISKRKFKM NTSSNEHPIS  241
VDTEIEILKK LDHPCIIKIE NFFDSEDFYY IVLELMEGGE LFDRVVNSTR LREPIAKLYF  301
YQMLLAVQYL HENGVIHRDL KPENVLLSST SEECCIKITD FGQSKILGET SLMRTLCGTP  361
TYLAPEVLNT AGTTGYSSAV DCWSLGVILF VCLGYPPFS EQNSNIPLKN QIAEGKYTYI  421
AAAWRNVSEQ AFDLVKNLLV VDPEQRLTTK QALEHPWLQD DSMKHTVERL MYGVDHTMPP  481
PIKKNIIRKR GHEWDQDAST SSCSEILPTS AEKRAKR
```

CHECKPOINT-ACTIVATING OLIGONUCLEOTIDES

RELATED APPLICATIONS

This application claims the benefit of priority to U.S. Application No. 60/202,028, filed May 4, 2000, herein incorporated by reference in its entirety.

FEDERAL GOVERNMENT SUPPORT

The research described herein was supported by grant number GM43974, awarded by the National Institutes of Health. The federal government may have certain rights in the invention.

FIELD OF THE INVENTION

The present invention relates generally to cell cycle progression and more specifically to molecules involved in regulating DNA replication checkpoints.

BACKGROUND OF THE INVENTION

DNA damage, if not properly repaired, results in genomic instability, which is highly mutagenic and potentially lethal to the cell. During the cell cycle, the integrity of chromosomal DNA is ensured by surveillance systems that sense damaged DNA and arrest the cell cycle, giving the cell more time for repair processes. The surveillance systems that inhibit the entry into mitosis in the presence of damaged (or unreplicated) DNA consist of checkpoint signaling pathways that ultimately regulate the Cdc2-cyclin B complex, also known as maturation or M-phase promoting factor (MPF). In various organisms, these pathways contain the phosphoinositide kinase (PIK) relatives ATM, ATR, Rad3, and Mec1, and the effector kinases Chk2, Cds1, Rad53, and Chk1. The phosphatase Cdc25 and kinases Wee1 and Myt1 directly control the inhibitory phosphorylation of Cdc2, which is maintained when upstream checkpoint regulators detect damaged or unreplicated DNA in the cell.

Although many types of DNA damage can activate a checkpoint, it is largely unknown what DNA structure is the ultimate damage signal. The radiomimetic agent methylmethane sulfonate (MMS), which elicits a strong Mec1-dependent checkpoint response in budding yeast, creates adducts and apurinic sites, which become single-and double-stranded breaks. Likewise, both UV and ionizing irradiation induce a DNA damage checkpoint in various organisms. UV causes the formation of pyrimidine dimers, which are repaired predominantly by nucleotide excision, whereas ionizing irradiation generates mainly double-stranded breaks. Since DNA damage can arise by multiple mechanisms and the processing of primary DNA lesions can be complex in eukaryotic cells, it has been difficult to characterize at a molecular level the DNA structures that elicit checkpoint responses.

In addition to DNA damage, DNA replication blocks can also trigger a cell cycle arrest. The signal(s) that elicits this arrest is unknown, but possibilities include replication intermediates, such as single-stranded DNA, which might accumulate when DNA synthesis is stalled. In budding yeast, the length of a cell cycle arrest in response to DNA damage correlates with the amount of the single-stranded DNA that is generated by endonucleolytic processing. Furthermore, the addition of single-stranded M13 DNA to Xenopus egg extracts results in a strong cell cycle delay.

Studies of the yeasts have revealed that DNA damage and replication blocks may be recognized by a group of proteins, each of which is required for a normal checkpoint. In the fission yeast *Schizosaccharomyces pombe*, for example, this group of gene products includes Rad1, Rad3, Rad9, Rad17, Rad26, Hus1, Cut5, and Crb2. Rad3 has substantial structural similarity to the human ATM and ATR proteins, each of which possesses protein kinase activity. A similar pathway exists in the budding yeast *Saccharomyces cerevisiae*. The biochemical functions of the other proteins in this group are poorly understood, but they are currently thought to be involved in sensing damaged DNA or stalled replication complexes. Cds1 and Chk1 are two effector kinases with overlapping functions that receive signals from upstream checkpoint sensors. DNA damage and replication blocks activate Cds1 by a mechanism that requires these proteins. Chk1, however, is normally activated in response to only DNA damage. Both Cds1 and Chk1 phosphorylate and inhibit the function of Cdc25, the protein phosphatase that dephosphorylates tyrosine-15 of the cyclin-dependent kinase Cdc2. Mammalian homologues of many of these checkpoint proteins have been isolated and have been shown to possess similar biochemical functions, indicating that many features of these checkpoint pathways have been conserved throughout evolution.

Xenopus egg extracts have been used to study vertebrate checkpoint mechanisms. Immunodepletion of a Xenopus homologue of Chk1 (Xchk1) results in a substantial but not complete abrogation of the cell cycle delay in Xenopus egg extracts in response to replication blocks induced by aphidicolin or to UV-damaged DNA. Xchk1 is involved in a caffeine-sensitive pathway, but that a caffeine-insensitive pathway is also involved in the response to aphidicolin and UV radiation. There is therefore a need to identify all key components of checkpoint pathways.

SUMMARY OF THE INVENTION

The present invention provides substantially pure polypeptides characterized as (a) phosphorylating Cdc25 or a homologue thereof; (b) having a molecular mass of about 58 kD; (c) having about 517 amino acids; (d) having SQ/TQ motifs at the amino terminal region; (e) having a carboxyl terminal kinase domain; and (f) having an amino terminal forkhead-associated domain.

Also provided by the invention is a substantially pure polypeptide having an amino acid sequence as set forth in SEQ ID NO:2 or conservative variants thereof.

Further provided by the invention is an isolated polynucleotide encoding a polypeptide polypeptides characterized as (a) phosphorylating Cdc25 or a homologue thereof; (b) having a molecular mass of about 58 kD; (c) having about 517 amino acids; (d) having SQ/TQ motifs at the amino terminal region; (e) having a carboxyl terminal kinase domain; and (f) having an amino terminal forkhead-associated domain. The invention also provides an isolated polynucleotide having the sequence set forth in SEQ ID NO: 1 and degenerate variants thereof The invention also provides isolated polynucleotides isolated polynucleotide selected from the group consisting of (a) a polynucleotide encoding a polypeptide having an amino acid sequence as set forth in SEQ ID NO:2; (b) a polynucleotide of (a), wherein all T's are U; and (c) a polynucleotide complementary to (a) or (b). Also provided are isolated polynucleotide fragments having at least 15 base pairs and that hybridizes to a polynucleotide encoding a polypeptide having the amino acid sequence set forth in SEQ ID NO:2.

Also provided by the present invention are isolated oligonucleotides having

GACTCCGAGAACCAATTGC (SEQ ID NO:3),.

GCAATTGGTTCTCGGAGTC (SEQ ID NO:4), and

GCGGCACGTTCTCGTGCCGC (SEQ ID NO:5).

The invention further provides an antibody that binds to a Cds1 polypeptide or immunoreactive fragments thereof Polyclonal and monoclonal antibodies are contemplated.

Also provided are methods for increasing mitotic delay in a vertebrate cell. The method includes providing to the cell one or more oligonucleotides that from double-stranded DNA.

Yet another embodiment of the invention provides a method for identifying a reagent that modulates phosphorylation of a polypeptide. The method includes incubating a reagent with the polypeptide, and one or more oligonucleotides that form double-stranded DNA, under conditions that allow the components to interact with each other; and comparing the phosphorylation of the polypeptide to phosphorylation of a polypeptide not incubated with the reagent, wherein a difference in phosphorylation is indicative of a reagent that modulates phosphorylation of the polypeptide. The modulation can be an increase in phosphorylation or a decrease in phosphorylation.

Yet a further embodiment of the invention provides a method for modulating cell cycle progression in a cell. The method includes providing to the cell a compound that affects the activity or expression of a Cds1 polypeptide, thereby modulating cell cycle progression.

Another embodiment of the invention provides a method of treating a subject having a cellular disorder associated with increased cell cycle progression compared to a subject not having the cellular disorder. The method includes administering to a subject having the disorder a therapeutically effective amount of a reagent that increases a Cds1 polypeptide activity, thereby treating the cellular disorder.

Yet another embodiment of the invention provides a method of diagnosing a Cds1-associated disorder in a subject. The method includes determining the level of Cds1 mRNA or protein expression in the subject, wherein a low level of Cds1 in the subject compared to the level in a subject not having a Cds-associated disorder is indicative of a Cds-associated disorder.

Also provided is a kit for activating a Cds1 polypeptide. The kit includes double-stranded DNA and a container for the DNA.

BRIEF DESCRIPTION OF THE DRAWINGS

FIG. 1 shows the nucleotide sequence of *Xenopus laevis* protein kinase Cds1 (Cds1) mRNA, complete cds (Accession Number AF174295; SEQ ID NO:1).

FIG. 2 shows the amino acid sequences of *Xenopus laevis* protein kinase Cds1 (Accession Number AAF75829; SEQ ID NO:2).

DETAILED DESCRIPTION OF THE INVENTION

Figure 3:
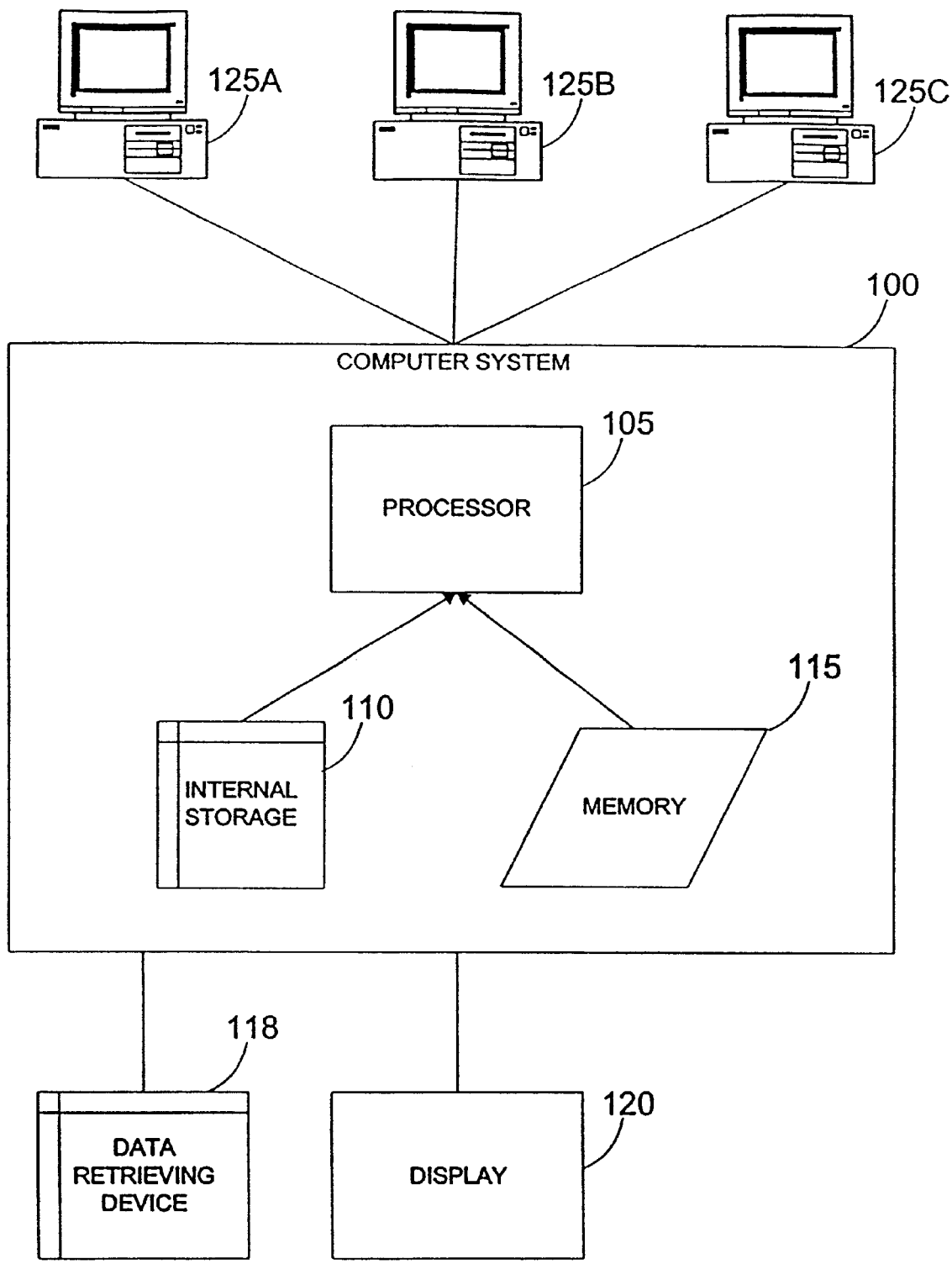
FIG. 3 is a flow diagram illustrating a computer system, data retrieving device and display.

The present invention provides polypeptides that are involved in regulating the progression of the cell cycle. The present invention is based on the discovery that a novel polypeptide, Cds1, plays a significant role in the DNA damage checkpoint. The Cds1 polypeptide is activated by double-stranded DNA and is phosphorylated in response to the presence of double-stranded DNA. Once activated, the polypeptide can phosphorylate Cdc25 polypeptides. The phosphorylation of the polypeptide and the following phosphorylation of Cdc25 polypeptides ensures that the timing of the cell cycle progression is appropriate.

When a cell encounters a problem such as damaged DNA or a block to replication, it can call upon a variety of mechanisms to fix the problem. But these mechanisms can take time, and it is often crucial that the cell does not continue through the cell cycle until the problem is fixed. That is where cell cycle checkpoints come in. The checkpoints recognize the problem and delay cell cycle progression by inhibiting the basic cell cycle machinery until the problem is fixed (Hartwell and Weinert, (1989) *Science* 246, 629–634; Elledge, (1996) *Science* 274, 1664–1672; Rhind and Russell, (1998) *Curr. Opin. Cell Biol.* 10, 749–58). These checkpoints can also regulate transcription and may directly regulate repair machinery. Many, if not all, of the major cell cycle transitions are regulated by one or another checkpoint. Checkpoints include DNA damage and replication checkpoints, which have served as the prototypic checkpoint pathways. These checkpoints are triggered by various forms of DNA damage, and various treatments that block replication, respectively.

One can divide checkpoints into three parts: a sensor, a transduction pathway and a target. The transduction pathways for the DNA damage and replication checkpoints are composed of a shared group of conserved proteins that may also serve as the sensors. The pathways have been recently reviewed (Elledge, (1996) supra; Longhese et al., (1998) *EMBO J.* 17, 5525–5528; Rhind and Russell, 1998, supra; Dasika et al., (1999) *Oncogene* 18, 7883–7899). Of the proteins known to be involved, one is a large protein kinase of the DNA-PK family, known as Rad3 in the fission yeast *Schizosaccharomyces pombe*, Mec1 in budding yeast *Saccharomyces cerevisiae*, MEI-41 in the fruit fly *Drosophila melanogaster*, and X-ATM in the frog *Xenopus laevis* (Zakian, 1995). Two homologues, ATM and ATR, have been identified in humans and mice (Westphal, 1997). For convenience, these homologues are referred to generically as ATMs but the specific name is used when referring to a specific organism. By analogy with DNA-PK, a kinase that is activated by binding to DNA ends, it is proposed that ATM acts to recognize the DNA damage or stalled replication forks and initiate the checkpoint signal (Hartley et al., (1995) *Cell* 82, 849–856; Bentley et al., (1996)*EMBO J.* 15, 6641–6651). The other members of this pathway could serve as regulatory subunits of a complex that has ATM as its core (Longhese et al., (1998) supra). Although it is appealing, there is little direct evidence for this model. However, the fact that the checkpoints share many upstream proteins suggests that they may recognize a similar or overlapping set of DNA structures. Downstream of ATM in each species are homologues of the Chk1 and Cds1 protein kinases (see for example, Weinert et al., (1994) *Genes Dev.* 8, 652–665; Kumagai et al., (1998). *J. Cell Biol.* 142, 1559–1569; Guo and Dunphy, (2000)*Mol. Biol. Cell* 11, 1535–1546, incorporated herein by reference; Liu et al., 2000b).

The founding member of the Cds1 family is budding yeast Rad53 (Allen et al., (1994) *Genes Dev.* 8, 2401–2415). Like Chk1, Rad53 is widely conserved (Murakami and Okayama, (1995) *Nature* 374, 817–819; Matsuoka et al., (1998) *Science* 282, 1893–1897; Blasina et al., (1999) *Curr. Biol.* 9, 1–10; Brown et al., (1999) *Proc. Natl. Acad. Sci. USA* 96, 3745–3750; Chaturvedi et al., (1999) *Oncogene* 18, 4047–4054; Tominaga et al., (1999) *J. Biol. Chem.* 274, 31463–31467; Guo and Dunphy, (2000) supra). These homologues are generally called Cds1, but the specific name is used when referring to a specific organism. The Cds1 homologues are recognizable by a similar kinase domain and an N-terminal forkhead associated (FHA) domain (Blasina et al., (1999) supra).

Accordingly, the present invention provides a substantially polypeptide characterized as (a) being phosphorylated in the presence of damaged double-stranded DNA; (b) phosphorylating Cdc25; (c) being activated by poly(dT)$_{40}$; (d) having a molecular mass of about 58 kD; (e) having about 517 amino acids; (f) having SQ/TQ motifs at the amino terminal region; (g) having a carboxyl terminal kinase domain; and (h) having an amino terminal forkhead-associated domain.

XCds1 becomes highly phosphorylated when M13 DNA or linearized, double-stranded plasmids are added to Xenopus egg extracts. Likewise, Cds1 undergoes checkpoint-associated phosphorylation in response to poly(dT)$_{40}$ and various double-stranded oligonucleotides (see Examples section). When M13 and poly(dT)$_{40}$ are added to the extracts in a single-stranded form, both of these templates are replicated very efficiently by the DNA synthetic machinery present in egg extracts and Cds1 is phosphorylated. Indeed, inhibition of M13 DNA replication by treatment with actinomycin D abolishes the modification of Cds1. Furthermore, various single-stranded oligonucleotides that are not replicated by egg extracts do not bring about the phosphorylation of Cds1.

Xcds1 undergoes checkpoint associated phosphorylation in the presence of double stranded oligonucleotides. For example, when isolated nucleotides having the sequence GACTCCGAGAACCAATTGC (SEQ ID NO:3) and GCAATTGGTTCTCGGAGTC (SEQ ID NO:4) are added to egg extracts containing Cds1, a double stranded DNA molecule is formed and Cds1 undergoes phosphorylation. Similarly, when an isolated oligonucleotide having the sequence GCGGCACGTTCTCGTGCCGC (SEQ ID NO:5) is added to egg extracts containing Cds1, phosphorylation of Cds1 ensues. The oligonucleotide sequence is capable of forming a hairpin structure by annealing (see underlined regions) and thus acts as double-stranded DNA.

Cds1 phosphorylates Cdc25, the protein phosphatase that dephosphorylates tyrosine 15 of Cdc2 (Zeng et al., (1998) Nature, 395, 507–510). When phosphorylated, Cdc25 activity is inhibited. Xcds1 possesses similar biochemical functions. Phosphorylation of Xenopus Cdc25 occurs on Serine residue 287 (Ser-287) in the 14-3-3 binding site of Xenopus Cdc25.

Xcds1 is activated by poly(dT)40. When Cds1 is phosphorylated in extracts containing poly (dT)$_{40}$, hyperphos-phorylated Cds1 shows a five- to six-fold increase over background in its kinase activity toward GST-Cdc25[254_316]-WT.

Cds1 polypeptides contain a relatively large number of SQ/TQ motifs at the amino terminal region. The serines (S) and threonines (T), each adjacent to a glutamine (Q) residue in this type of motif, are potential substrates for kinases such as ATM, ATR, and DNX-PK that are involved in checkpoint pathways (Kim et al., (1999) *J. Biol. Chem.* 274, 37538–37543).

Cds1 is further characterized as having a carboxyl terminal kinase domain. This region is the most conserved region of Xcds1 when compared to Chk2, the human homologue of Cds1.

Xcds1 is also characterized as having an amino terminal forkhead-assoicated domain (FHA domain). FHA domains, originally recognized in the forkhead transcription factor, are believed to act as protein—protein interaction domains, and in some instances bind specifically to phosphorylated partners (Hofmann and Bucher, (1995) *Trends Biochem. Sci.* 20, 347–349; Sun et al., (1998) *Science* 281, 272–274; Durocher et al., (1999) *Mol. Cell* 4, 387–394.

An exemplary Xcds1 polypeptide is set forth in SEQ ID NO:2. The invention includes conservative variants thereof. The terms "conservative variation" and "substantially similar" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The terms "conservative variation" and "substantially similar" also include the use of a substituted amino acid in place of an unsubstituted parent amino acid provided that antibodies raised to the substituted polypeptide also immunoreact with the unsubstituted polypeptide.

In one embodiment of the invention, the polypeptide is identical with or homologous to a Xenopus Cds1 polypeptide, such as a mammalian Cds1 polypeptide. For instance, the Cds1 polypeptide preferably has an amino acid sequence at least 80% homologous to a polypeptide represented by SEQ ID No:2, though polypeptides with higher sequence homologies of, for example, 85%, 90% or 95% are also embraced by the invention. The Xcds polypeptides can comprise a full length protein, such as represented in the sequence listing, or it can comprise a fragment of, for instance, at least 5, 10, 20, 50, 100, 150 or 200 amino acids in length.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid sequence encoding a Cds1 polypeptide" may thus refer to one or more genes within a particular individual. Moreover, individual organisms may bear different nucleotide sequences, called alleles, which code for substantially the same polypeptide. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. Homology can be shown by alignment of sequences, using for example the Pretty Plot function of the GCG program. PRETTYPLOT displays multiple sequence alignments and calculates a consensus sequence. PRETTYPLOT prints and plots sequences with their columns aligned. This utility is used after a number of sequences have had gaps added to make them all align. PRETTYPLOT's output allows one to look at relationships among several sequencesAn "unrelated" or "non-homologous" sequence shares less than 25 percent identity, though preferably less than 15 percent identity, with one of the Cds1 sequences of the present invention.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject Cds1 polypeptides preferably includes no more than 10 kilobases (kb) of nucleic acid sequence which naturally immediately flanks the Xcds1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Exemplary polynucleotides encoding a Cds1 polypeptide is set forth in SEQ ID NO:1. The term "polynucleotide", "nucleic acid", "nucleic acid sequence", or "nucleic acid molecule" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or genomic DNA) independent of other sequences. It also includes genomic DNA which refers to a contiguous sequence of nucleotide that includes one or more protein coding regions, introns, upstream and downstream regulatory sequences, i.e., non-coding 5'- and 3'-regulatory sequences. Thus, the term "polynucleotide encoding a polypeptide" encompasses a polynucleotide which includes coding sequence for the polypeptide as well as a polynucleotide which includes additional coding and/or non-coding sequence.

The invention also provides an isolated polynucleotide having at least 15 continuous base pairs that hybridizes to a polynucleotide selected from the group consisting of (a) a polynucleotide encoding a polypeptide having an amino acid sequence as set forth in amino acids 1 to 86 or amino acids 461 to 517 of SEQ ID NO:2; (b) a polynucleotide of (a), wherein T can be U; (c) a polynucleotide complementary to (a) or (b); (d) a polynucleotide having a nucleotide sequence as set forth in nucleotides 224 to 481 or nucleotides 1604 to 1770 of SEQ ID NO:1; and (e) degenerate variants of (a), (b), (c) or (d).

The nucleotides of the invention can be deoxyribonucleotides, ribonucleotides in which uracil (U) is present in place of thymine (T), or modified forms of either nucleotide. The nucleotides of the invention can be complementary to the deoxynucleotides or to the ribonucleotides. A polynucleotide encoding a Cds protein includes "degenerate variants", sequences that are degenerate as a result of the genetic code. There are 20 naturally occuring amino acids, most of which are specified by more than one codon. Therefore, all degenerate nucleotide sequences are included in the invention as long as the amino acid sequence of a polypeptide encoded by the nucleotide sequence of SEQ ID NO: 1 is functionally unchanged.

A nucleic acid molecule encoding a Cds1 protein includes sequences encoding functional Cds1 polypeptides as well as functional fragments thereof. As used herein, the term "functional polypeptide" refers to a polypeptide which possesses biological function or activity which is identified through a defined functional assay (e.g., Examples Section), and which is associated with a particular biologic, morphologic, or phenotypic alteration in the cell, for example an alteration in the timing of the cell cycle. The term "functional fragments of Xcds1 protein" refers to fragments of a Xcds1 protein that retain a XCds1 activity, e.g., the ability to be phophorylated in the presence of double-stranded DNA, being able to phosphorylate Cdc25, and the like. Additionally, functional Xcds1 fragments may act as competitive inhibitors of Xcds1 binding, for example. Biologically functional fragments, for example, can vary in size from a polypeptide fragment as small as an epitope capable of binding an antibody molecule to a large polypeptide capable of participating in the characteristic induction or programming of biological changes within a cell. Nucleotide fragments of the invention have at least 15 base pairs, preferably 20 base pairs, and hybridize to a polynucleotide encoding a polypeptide as set forth in SEQ ID NO:2.

Yet another embodiment of the invention provides an isolated polynucleotide, wherein the nucleotide is at least 15 base pairs in length which hybridizes under moderately to highly stringent conditions to DNA encoding a polypeptide as set forth in SEQ ID NO:2. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderately stringent conditions); and 0.1×SSC at about 68° C. (highly stringent conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ. ID No. 1, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a Cds1-encoding nucleic acid in a sample of cells isolated from a patient; e.g. for measuring the mRNA level in a cell.

Another aspect of the invention includes an isolated oligonucleotide having the sequence GACTCCGAGAACCAATTGC (SEQ ID NO:3). A further embodiment of the invention includes an isolated oligonucleotide having the sequence GCAATTGGTTCTCGGAGTC (SEQ ID NO:4). Yet another embodiment of the invention includes an isolated oligonucleotide having the sequence GCGGCACGTTCTCGTGCCGC (SEQ ID NO:5).

Antibodies of the invention may bind to Cds1 polypeptides provided by the invention to prevent normal interactions of Cds1 proteins. Binding of antibodies to Cds1 proteins can interfere with, for example, cell cycle progression. Binding of antibodies can interfere with Xcds1 protein phosphorylation of a cdc25 protein, and the like.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "antibody" as used in this invention includes intact molecules as well as fragments thereof, such as Fab, F(ab')2, and Fv which are capable of binding to an epitopic determinant present in an invention polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, N.Y. (1988), incorporated herein by reference). Monoclonal antibodies are made from antigen containing fragments of the protein by methods well known to those skilled in the art (Kohler & Milstein, *Nature* 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Briefly, monoclonal antibodies can be obtained by injecting mice with a composition comprising an antigen/ligand, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)" in *Methods In Molecular Biology*, Vol. 10, pages 79–104 (Humana Press 1992).

Antibodies that bind to an invention polypeptide can be prepared using an intact polypeptide or fragments containing small peptides of interest as the immunizing antigen. For example, it may be desirable to produce antibodies that specifically bind to the amino- or carboxyl-terminal domains of an invention polypeptide. For the preparation of polyclonal antibodies, the polypeptide or peptide used to immunize an animal is derived from translated cDNA or chemically synthesized and can be conjugated to a carrier protein, if desired. Commonly used carrier proteins which may be chemically coupled to the immunizing peptide include keyhole limpet hemocyanin (KLH), thyroglobulin, bovine serum albumin (BSA), tetanus toxoid, and the like.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See, for example, Coligan, et al., Unit 9, Current Protocols in Immunology, Wiley Interscience, 1994, incorporated herein by reference).

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique that may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal and polyclonal antibodies of the invention for the in vivo detection of antigen, e.g., a Cds1 protein, the detectably labeled antibody is given a dose which is diagnostically effective. The term "diagnostically effective" means that the amount of detectably labeled antibody is administered in sufficient quantity to enable detection of the site having the antigen comprising a polypeptide of the invention for which the antibodies are specific.

The concentration of detectably labeled antibody which is administered should be sufficient such that the binding to those cells having the polypeptide is detectable compared to the background. Further, it is desirable that the detectably labeled antibody be rapidly cleared from the circulatory system in order to give the best target-to-background signal ratio.

As a rule, the dosage of detectably labeled antibody for in vivo treatment or diagnosis will vary depending on such factors as age, sex, and extent of disease of the individual. Such dosages may vary, for example, depending on whether multiple injections are given, antigenic burden, and other factors known to those of skill in the art.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

A polynucleotide useful in a method of the invention also can be operatively linked to tissue specific regulatory element. For example, a neuron specific regulatory element can be employed such that expression of an encoded peptide agent is restricted to neurons in an individual, or to neurons in a mixed population of cells in culture, for example, an organ culture. For example, neuronal promoters such as the myelin basic protein promoter and other neuronal-specific promotes known to those of skill in the art may be used. Muscle-regulatory elements including, for example, the muscle creatine kinase promoter (Sternberg et al., *Mol. Cell.* *Biol.* 8:2896–2909, 1988, which is incorporated herein by reference) and the myosin light chain enhancer/promoter (Donoghue et al., *Proc. Natl. Acad. Sci., USA* 88:5847–5851, 1991, which is incorporated herein by reference) are well known in the art. A variety of other promoters have been identified which are suitable for up regulating expression in cardiac tissue. Included, for example, are the cardiac I-myosin heavy chain (AMHC) promoter and the cardiac I-actin promoter. Other examples of tissue-specific regulatory elements include, tissue-specific promoters, pancreatic (insulin or elastase), and actin promoter in smooth muscle cells. Through the use of promoters, such as milk-specific promoters, recombinant retroviruses may be isolated directly from the biological fluid of the progeny.

A Cds1 polynucleotide of the invention can be inserted into a vector, which can be a cloning vector or a recombinant expression vector. The term "expression vector" refers to a plasmid, virus or other vehicle known in the art that has been manipulated by insertion or incorporation of a polynucleotide, particularly, with respect to the present invention, a polynucleotide encoding all or a peptide portion of a CDs1 protein. Such expression vectors contain a promoter sequence, which facilitates the efficient transcription of the inserted genetic sequence of the host. The expression vector generally contains an origin of replication, a promoter, as well as specific genes, which allow phenotypic selection of the transformed cells. Vectors suitable for use in the present invention include, but are not limited to, the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter, which can be a T7 promoter, metallothionein I promoter, polyhedrin promoter, or other promoter as desired, particularly tissue specific promoters or inducible promoters.

Viral expression vectors can be particularly useful for introducing a polynucleotide useful in a method of the invention into a cell, particularly a cell in a subject. Viral vectors provide the advantage that they can infect host cells with relatively high efficiency and can infect specific cell types. For example, a polynucleotide encoding a Cds1 protein or functional peptide portion thereof can be cloned into a baculovirus vector, which then can be used to infect an insect host cell, thereby providing a means to produce large amounts of the encoded protein or peptide portion. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpes virus vectors, vaccinia virus vectors, and the like (see Miller and Rosman, *BioTechniques* 7:980–990, 1992; Anderson et al., *Nature* 392:25–30 *Suppl.*, 1998; Verma and Somia, *Nature* 389:239–242, 1997; Wilson, *New Engl. J. Med.* 334:1185–1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

A polynucleotide sequence encoding a Cds1 protein can be expressed in either prokaryotes or eukaryotes. Hosts can include microbial, yeast, insect and mammalian organisms. Methods of expressing polynucleotides having eukaryotic or viral sequences in prokaryotes are well known in the art, as are biologically functional viral and plasmid DNA vectors capable of expression and replication in a host. Methods for constructing an expression vector containing a polynucleotide of the invention are well known, as are factors to be considered in selecting transcriptional or translational control signals, including, for example, whether the polynucleotide is to be expressed preferentially in a particular cell type or under particular conditions (see, for example, Sambrook et al., supra, 1989).

A variety of host cell/expression vector systems can be utilized to express a Cds1 polypeptide coding sequence, including, but not limited to, microorganisms such as bacteria transformed with recombinant bacteriophage DNA, plasmid DNA or cosmid DNA expression vectors; yeast cells transformed with recombinant yeast expression vectors; plant cell systems infected with recombinant virus expression vectors such as a cauliflower mosaic virus or tobacco mosaic virus, or transformed with recombinant plasmid expression vector such as a Ti plasmid; insect cells infected with recombinant virus expression vectors such as a baculovirus; animal cell systems infected with recombinant virus expression vectors such as a retrovirus, adenovirus or vaccinia virus vector; and transformed animal cell systems genetically engineered for stable expression. Where the expressed Cds1 protein is post-translationally modified, for example, by glycosylation, it can be particularly advantageous to select a host cell/expression vector system that can effect the desired modification, for example, a mammalian host cell/expression vector system.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516–544, 1987). For example, when cloning in bacterial systems, inducible promoters such as pL of bacteriophage λ, plac, ptrp, ptac (ptrp-lac hybrid promoter) and the like can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

In yeast cells, a number of vectors containing constitutive or inducible promoters can be used (see Ausubel et al., supra, 1987, see chapter 13; Grant et al., *Meth. Enzymol.* 153:516–544, 1987; Glover, *DNA Cloning Vol. II (IRL Press,* 1986), see chapter 3; Bitter, *Meth. Enzymol.* 152:673–684, 1987; see, also, *The Molecular Biology of the Yeast Saccharomyces* (Eds., Strathern et al., Cold Spring Harbor Laboratory Press, 1982), Vols. I and II). A constitutive yeast promoter such as ADH or LEU2 or an inducible promoter such as GAL can be used (Rothstein, *DNA Cloning* Vol. II (supra, 1986), chapter 3). Alternatively, vectors can be used which promote integration of foreign DNA sequences into the yeast chromosome.

Eukaryotic systems, particularly mammalian expression systems, allow for proper post-translational modifications of expressed mammalian proteins. Eukaryotic cells which possess the cellular machinery for proper processing of the primary transcript, glycosylation, phosphorylation, and advantageously, plasma membrane insertion of the gene product can be used as host cells for the expression of a Cds1 protein, or functional peptide portion thereof Mammalian cell systems which utilize recombinant viruses or viral elements to direct expression can be engineered. For example, when using adenovirus expression vectors, the Cds1 polypeptide coding sequence can be ligated to an adenovirus transcription/translation control complex, e.g., the late promoter and tripartite leader sequence. Alternatively, the vaccinia virus 7.5K promoter can be used (Mackett et al., *Proc. Natl. Acad. Sci., USA* 79:7415–7419, 1982; Mackett et al., *J. Virol.* 49:857–864, 1984; Panicali et al., *Proc. Natl. Acad. Sci., USA* 79:4927–4931, 1982). Particularly useful are bovine papilloma virus vectors, which can replicate as extrachromosomal elements (Sarver et al., *Mol. Cell. Biol.* 1:486, 1981).

Shortly after entry of this DNA into mouse cells, the plasmid replicates to about 100 to 200 copies per cell. Transcription of the inserted cDNA does not require integration of the plasmid into the host cell chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the Cds1 protein gene in host cells (Cone and Mulligan, *Proc. Natl. Acad. Sci., USA* 81:6349–6353, 1984). High level expression can also be achieved using inducible promoters, including, but not limited to, the metallothionein IIA promoter and heat shock promoters.

For long term, high yield production of recombinant proteins, stable expression is preferred. Rather than using expression vectors which contain viral origins of replication, host cells can be transformed with Cds1 protein cDNA controlled by appropriate expression control elements such as promoter, enhancer, sequences, transcription terminators, and polyadenylation sites, and a selectable marker. The selectable marker in the recombinant plasmid can confer resistance to the selection, and allows cells to stably integrate the plasmid into their chromosomes and grow to form foci, which, in turn can be cloned and expanded into cell lines. For example, following the introduction of foreign DNA, engineered cells can be allowed to grow for 1 to 2 days in an enriched media, and then are switched to a selective media. A number of selection systems can be used, including, but not limited to, the herpes simplex virus thymidine kinase (Wigler et al., *Cell* 11:223, 1977), hypoxanthine-guanine phosphoribosyltransferase (Szybalska and Szybalski, *Proc. Natl. Acad. Sci., USA* 48:2026, 1982), and adenine phosphoribosyltransferase (Lowy, et al., *Cell* 22:817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Proc. Natl. Acad. Sci. USA* 77:3567, 1980; O'Hare et al., *Proc. Natl. Acad. Sci., USA* 78: 1527, 1981); gpt, which confers resistance to mycophenolic acid (Mulligan and Berg, *Proc. Natl. Acad. Sci., USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984) genes. Additional selectable genes, including trpB, which allows cells to utilize indole in place of tryptophan; hisD, which allows cells to utilize histinol in place of histidine (Hartman and Mulligan, *Proc. Natl. Acad. Sci., USA* 85:8047, 1988); and ODC (ornithine decarboxylase) which confers resistance to the ornithine decarboxylase inhibitor, 2-(difluoromethyl)-DL-ornithine, DFMO (McConlogue, *Curr. Comm. Mol. Biol.* (Cold Spring Harbor Laboratory Press, 1987), also have been described.

When the host is a eukaryote, such methods of transfection of DNA as calcium phosphate co-precipitates, conventional mechanical procedures such as microinjection, electroporation, insertion of a plasmid encased in liposomes, or virus vectors can be used. Eukaryotic cells can also be cotransformed with DNA sequences encoding the Cds1 proteins of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Gluzman, *Eukaryotic Viral Vectors* (Cold Spring Harbor Laboratory Press, 1982)).

The invention provides a method for producing a polypeptide encoded by the nucleotide sequence of SEQ ID NO:1 or fragments thereof, including culturing the host cell under conditions suitable for the expression of the polypeptide and recovering the polypeptide from the host cell culture.

A Cds1 polypeptide or a fragment thereof, can be encoded by a recombinant or non-recombinant nucleic acid molecule and expressed in a cell. Preparation of an Cds1 polypeptide by recombinant methods provides several advantages. In particular, the nucleic acid sequence encoding the Cds1 polypeptide can include additional nucleotide sequences encoding, for example, peptides useful for recovering the Cds1 polypeptide from the host cell. A Cds1 polypeptide can be recovered using well known methods, including, for example, precipitation, gel filtration, ion exchange, reverse-phase, or affinity chromatography (see, for example, Deutscher et al., *Guide to Protein Purification in Meth. Enzymol.*, Vol. 182, (Academic Press, 1990)). Such methods also can be used to purify a fragment of an polypeptide, for example, a particular binding sequence, from a cell in which it is naturally expressed.

A recombinant nucleic acid molecule encoding an Cds1 polypeptide or a fragment thereof can include, for example, a protease site, which can facilitate cleavage of the Cds1 polypeptide from a non-Cds1 polypeptide sequence, for example, a tag peptide, secretory peptide, or the like. As such, the recombinant nucleic acid molecule also can encode a tag peptide such as a polyhistidine sequence, a FLAG peptide (Hopp et al., *Biotechnology* 6:1204 (1988)), a glutathione S-transferase polypeptide or the like, which can be bound by divalent metal ions, a specific antibody (U.S. Pat. No. 5,011,912), or glutathione, respectively, thus facilitating recovery and purification of the Cds1 polypeptide comprising the peptide tag. Such tag peptides also can facilitate identification of the Cds1 polypeptide through stages of synthesis, chemical or enzymatic modification, linkage, or the like. Methods for purifying polypeptides comprising such tags are well known in the art and the reagents for performing such methods are commercially available.

A nucleic acid molecule encoding a Cds1 polypeptide can be engineered to contain one or more restriction endonuclease recognition and cleavage sites, which can facilitate, for example, substitution of an element of the Cds1 polypeptide such as the selective recognition domain or, where present, a spacer element. As such, related Cds1 polypeptides can be prepared, each having a similar activity, but having specificity for different function-forming contexts. A restriction endonuclease site also can be engineered into (or out of) the sequence coding a peptide portion of the Xcdss1 polypeptide, and can, but need not change one or more amino acids encoded by the particular sequence. Such a site can provide a simple means to identify the nucleic acid sequence, based on cleavage (or lack of cleavage) following contact with the relevant restriction endonuclease, and, where introduction of the site changes an amino acid, can further provide advantages based on the substitution.

In another series of embodiments, the present invention provides transgenic animal models diseases or disorders associated with mutations in the Cds1 protein genes. The animal may be essentially any reptile, fish, mammal, and the like. Preferably, the transgenic animal is mammalian including rats, mice, hamsters, guinea pigs, rabbits, dogs, cats, goats, sheep, pigs, and non-human primates. In addition, invertebrate models, including nematodes and insects, may be used for certain applications. The animal models are produced by standard transgenic methods including microinjection, transfection, or by other forms of transformation of embryonic stem cells, zygotes, gametes, and germ line cells with vectors including genomic or cDNA fragments, minigenes, homologous recombination vectors, viral insertion vectors and the like. Suitable vectors include vaccinia virus, adenovirus, adeno associated virus, retrovirus, liposome transport, neurotropic viruses, herpes simplex virus, and the like. The animal models may include transgenic sequences comprising or derived from Cds1 proteins including normal and mutant sequences, intronic, exonic and untranslated sequences, and sequences encoding subsets of Cds1 proteins such as functional domains.

The major types of animal models provided include: (1) Animals in which a normal human Cds1 gene has been recombinantly introduced into the genome of the animal as an additional gene, under the regulation of either an exogenous or an endogenous promoter element, and as either a minigene or a large genomic fragment; in which a normal human Cds1 gene has been recombinantly substituted for one or both copies of the animal's homologous Cds1 gene by homologous recombination or gene targeting; and/or in which one or both copies of one of the animal's homologous Cds1 genes have been recombinantly "humanized" by the partial substitution of sequences encoding the human homologue by homologous recombination or gene targeting. (2) Animals in which a mutant Cds1 gene has been recombinantly introduced into the genome of the animal as an additional gene, under the regulation of either an exogenous or an endogenous promoter element, and as either a minigene or a large genomic fragment; in which a mutant Cds1 gene has been recombinantly substituted for one or both copies of the animal's homologous Cds1 gene by homologous recombination or gene targeting; and/or in which one or both copies of one of the animal's homologous Cds1 genes have been recombinantly "humanized" by the partial substitution of sequences encoding a mutant human homologue by homologous recombination or gene targeting. (3) Animals in which a mutant version of one of that animal's Cds1 genes has been recombinantly introduced into the genome of the animal as an additional gene, under the regulation of either an exogenous or an endogenous promoter element, and as either a minigene or a large genomic fragment; and/or in which a mutant version of one of that animal's Cds1 genes has been recombinantly substituted for one or both copies of the animal's homologous Cds1 gene by homologous recombination or gene targeting. (4) "Knockout" animals in which one or both copies of one of the animal's Cds1 genes have been partially or completely deleted by homologous recombination or gene targeting, or have been inactivated by the insertion or substitution by homologous recombination or gene targeting of exogenous sequences.

In a preferred embodiment of the invention, there is provided a transgenic non-human animal having a transgene that expresses a Cds1-encoding polynucleotide chromosomally integrated into the germ cells of the animal. Animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, Jan. 12, 1994) can be utilized whereby the embryo is obtained from a sacrificed hen approximately two and one-half h after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The non-human animals of the invention are murine typically (e.g., mouse). The transgenic non-human animals of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionine, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, (1976) *Proc. Natl. Acad. Sci USA* 73:1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y). The viral vector system used to introduce the transgene is typically a replication-defective retro virus carrying the transgene (Jahner, et al., (1985) *Proc. Natl. Acad. Sci. USA* 82:6927–6931; Van der Putten, et al., (1985) *Proc. Natl. Acad. Sci USA* 4 82:6148–6152,). Transfection is easily and efficiently obtained by culturing the blastomeres on a monolayer of virus-producing cells (Van der Putten, supra; Stewart, et al., (1987) *EMBO J.* 6:383–388). Alternatively, infection can be performed at a later stage. Virus or virus-producing cells can be injected into the blastocoel (Jahner et al. (1982) *Nature* 298:623–628). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode Cds1 polypeptide-sense and anti-sense polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. As used herein, the term "transgenic" includes any transgenic technology familiar to those in the art which can produce an organism carrying an introduced transgene or one in which an endogenous gene has been rendered non-functional or "knocked out".

Another embodiment of the invention provides a computer readable medium having store thereon a nucleic acid sequence selected from the group consisting of SEQ ID NO:1 and sequences substantially identical thereto, or a polypeptide sequence selected from the group consisting of SEQ ID NO:2 and sequences substantially identical thereto.

A further embodiment of the invention provides a computer system comprising a processor and a data storage device wherein said date storage device has stored thereon a nucleic acid sequence selected from the group consisting of SEQ ID NO:1, and sequences substantially identical thereto, or a polypeptide sequence selected from the group consisting of SEQ ID NO:2, and sequences substantially identical thereto. The computer system, additionally can contain a sequence comparison algorithm and a data storage device having at least one reference sequence stored on it. The sequence comparison algorithm comprises a computer program which indicates polymorphisms. The term "polymorphism", as used herein, refers to the existence of multiple alleles at a single locus. Polymorphism can be are several types including, for example, those that change DNA sequence but do not change protein sequence, those that change protein sequence without changing function, those that create proteins with a different activity, and those that create proteins that are non-functional.

Embodiments of the invention include systems (e.g., internet based systems), particularly computer systems which store and manipulate the coordinate and sequence information described herein. One example of a computer system 100 is illustrated in block diagram form in FIG. 3. As used herein, "a computer system" refers to the hardware components, software components, and data storage components used to analyze coordinates and sequences information. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a–c in a network or wide area network to provide centralized access to the computer system 100.

Figure 4:
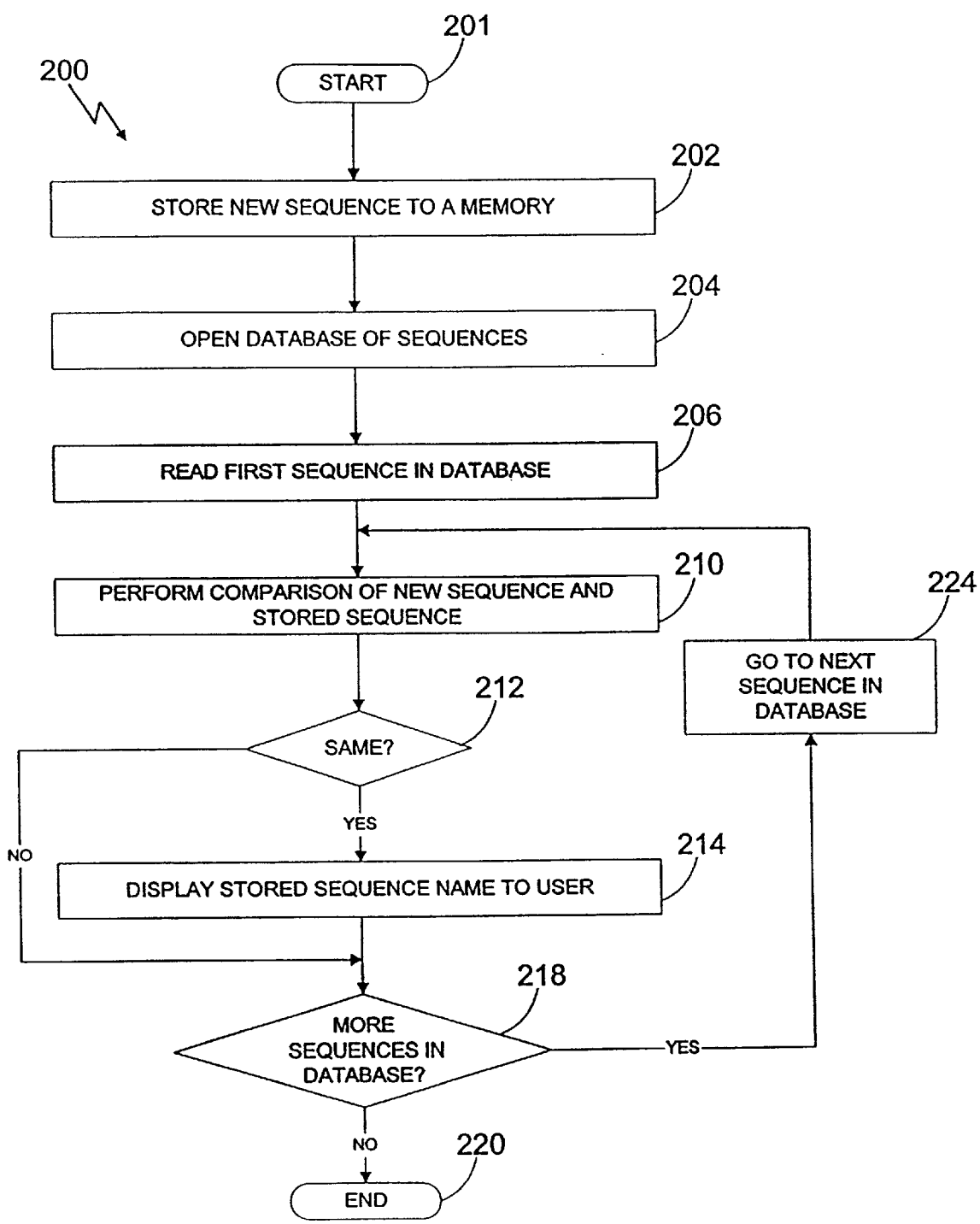
FIG. 4 is a flow diagram illustrating one embodiment of process 200 for comparing a new nucleotide or protein sequence with a database of sequences in order to determine the homology levels between the new sequence and the sequences in the database.

FIG. 4 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Figure 5:
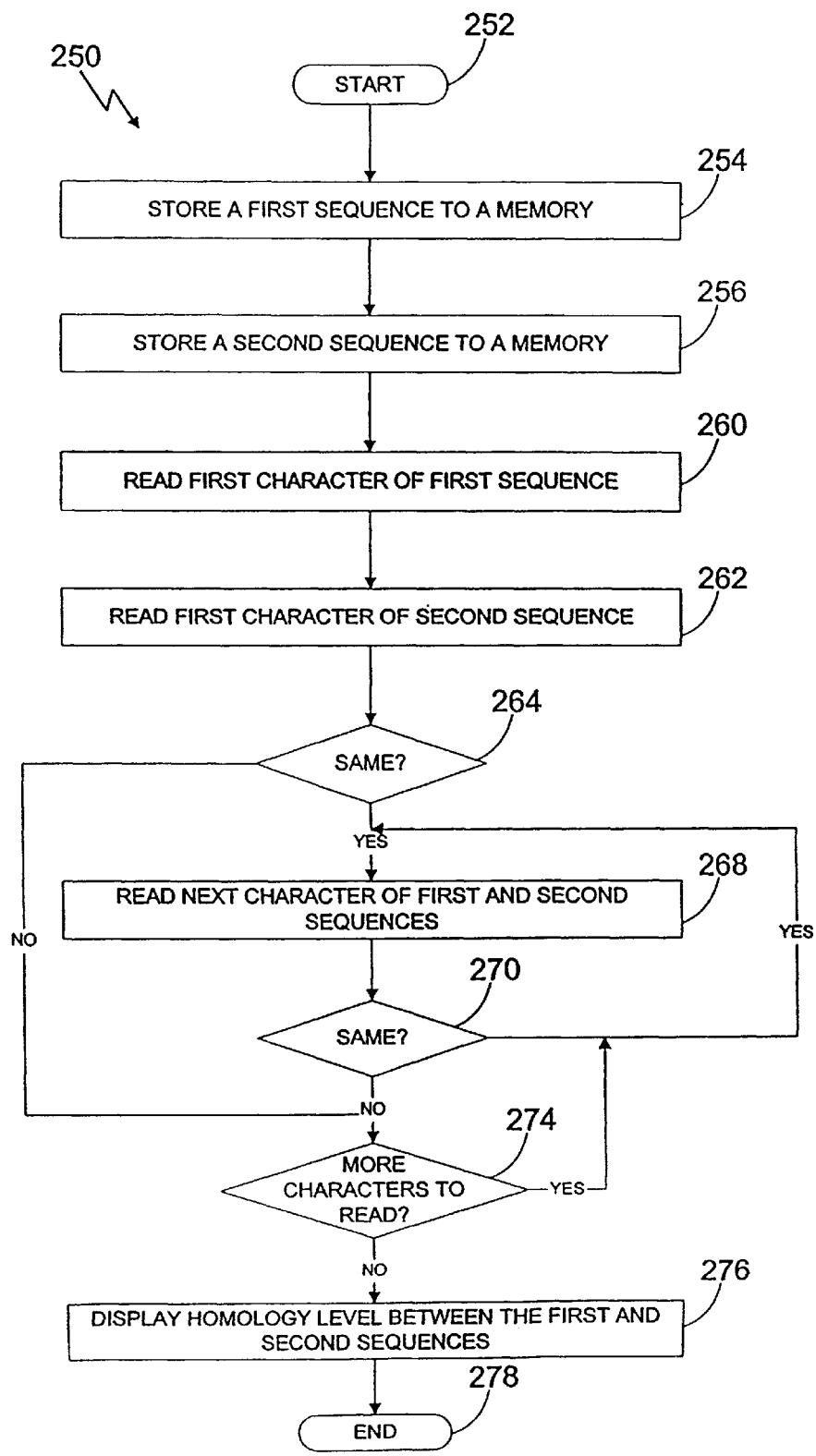
FIG. 5 is a flow diagram illustrating one embodiment of a process 250 in a computer for determining whether two sequences are homologous.
Figure 6:
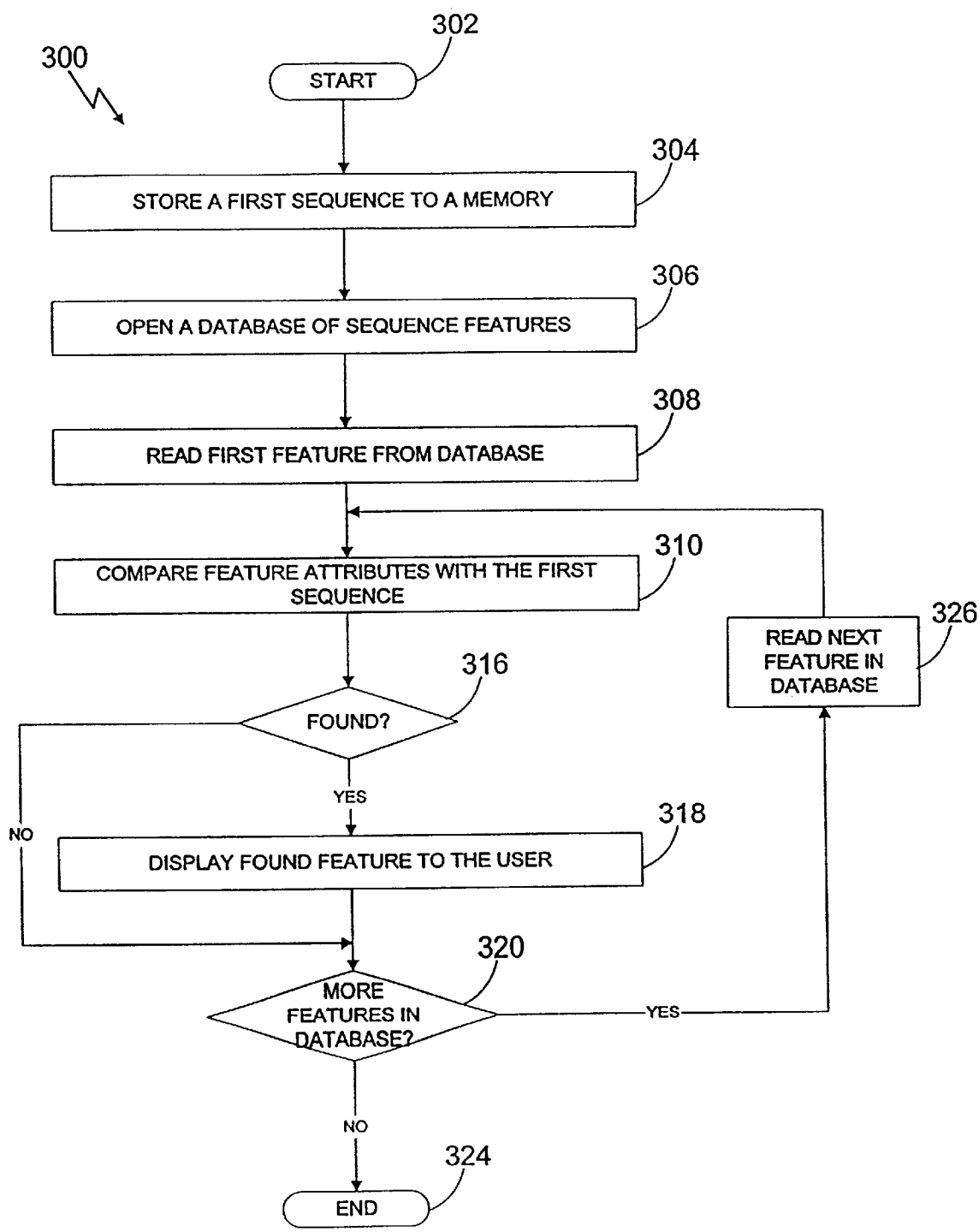
FIG. 6 is a flow diagram illustrating one embodiment of a process 300 for comparing features in polynucleotide and polypeptide sequences.

FIG. 5 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (see J. Roach, at the uniform resource locator (url) weber.u.Washington.edu/~roach/human_genome_progress 2.html) (Gibbs, 1995). At least twenty-one other genomes have already been sequenced, including, for example, *M. genitalium* (Fraser et al., 1995), M. jannaschii (Bult et al., 1996), *H. influenzae* (Fleischmann et al., 1995), *E. coil* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis sp.* Several databases containing genomic information annotated with some functional information are maintained by different organization, and are accessible via the internet at world wide web sites such as: tigr.org/tdb; .genetics.wisc.edu; .genome-.stanford.edu/~ball; hiv-web.lanl.gov; ncbi.nlm.nih.gov; ebi.ac.uk; Pasteur.fr/other/biology; and genone.wi.mit.edu.

One example of a useful algorithm is BLAST and BLAST 2.0 algorithms, which are described in Altschul et al., Nuc. Acids Res. 25:3389–3402, 1977, and Altschul et al., J. Mol. Biol. 215:403–410, 1990, respectively. Software for performing BLAST analyses is publicly available through the National Center for Biotechnology Information (NCBI; world wide web address ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., *Science* 256:1443–1445, 1992; Henikoff and Henikoff, *Proteins* 17:49–61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine site on the world wide web, for example.

The parameters used with the above algorithms may be adapted depending on the sequence length and degree of homology studied. In some embodiments, the parameters may be the default parameters used by the algorithms in the absence of instructions from the user.

A method is provided for identifying a reagent that phosphorylation of a Cds1 polypeptide. The method includes incubating the reagent with a Cds1 polypeptide, and one or more oligonucleotides that can form double-stranded DNA under conditions sufficient to permit the components to interact with each other, and comparing the phosphorylation status of the Cds1 polypeptide incubated with the reagent with the phosphorylation status of a Cds1 polypeptide not incubated with the reagent.

Modulation of phosphorylation may be an increase in phosphorylation or a decrease in phosphorylation. Various amino acid residues can be phosphorylated. Phosphorylation is the addition of a phosphate group, e.g. $PO_4$, by esterification with the hydroxyl group of an amino acid. Amino acids serine and threonine are typically phosphorylated with serine preferred.

The reagent can be selected from the species consisting of a peptide, a peptidomimetic, a polypeptide, a pharmaceutical, a chemical compound, an oligonucleotide, a polynucleotide and an antibody.

When the Cds1 polypeptide is Xenopus Cds1, a reagent includes one or more oligonucleotides. In one embodiment of the invention oligonucleotides having the sequences set forth in SEQ ID NO:3 and SEQ ID NO:4 modulate phosphorylation. In another embodiment of the invention, a nucleotide having the sequence set forth in SEQ ID NO:5 modulates phosphorylation. Any oligonucleotides that can form a double-stranded DNA molecule can modulate phosphorylation of Cds1.

Also provided by the invention is a method of modulating cell cycle progression in a cell. The method includes providing to the cell a reagent that affects the activity or expression of a Cds1 polypeptide. Modulation of cell cycle progression can be a speeding up of the cell cycle or it may be an inhibition or reduction in the progression of the cell cycle. An inhibition of the cell cycle can include an increase in the time a cell is in a gap phase, e.g., G0, the pause after mitosis, G1, the gap after mitosis before DNA synthesis starts or G2, the gap after DNA synthesis is complete and before mitosis and cell division begins. The gap phases allow for checkpoints, stopping points in the cell cycle where progress can be halted. During this time, cellular mechanisms insure that DNA is not damaged, or incompletely or incorrectly replicated. Speeding up the cell cycle could allow rounds of mitosis to proceed in a shorter period of time. This may result in damaged DNA which, following mitosis, could have serious or fatal effects for the daughter cells.

Any Cds1 protein may be employed in invention methods. In certain embodiments a Xenopus Cds1 protein according to the amino acid sequence set forth in SEQ ID NO:2 is used.

The cell may be any cell of interest, including but not limited to neuronal cells, glial cells, cardiac cells, bronchial cells, uterine cells, testicular cells, liver cells, renal cells, intestinal cells, cells from the thymus and spleen, placental cells, endothelial cells, endocrine cells including thyroid, parathyroid, pituitary and the like, smooth muscle cells and skeletal muscle cells. The term "incubating" includes conditions which allow contact between the test compound and the cell of interest. "Contacting" may include in solution or in solid phase.

Reagents which modulate cell cycle progression can include peptides, peptidomimetics, polypeptides, pharmaceuticals, chemical compounds and biological agents, for example. Antibodies and combinatorial compound libraries can also be tested using the method of the invention. One class of organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

The test agent may also be a combinatorial library for screening a plurality of compounds. Compounds such as peptides identified in the method of the invention can be further cloned, sequenced, and the like, either in solution of after binding to a solid support, by any method usually applied to the isolation of a specific DNA sequence Molecular techniques for DNA analysis (Landegren et al., *Science* 242:229–237, 1988) and cloning have been reviewed (Sambrook et al., *Molecular Cloning: a Laboratory Manual*, 2nd Ed.; Cold Spring Harbor Laboratory Press, Plainview, N.Y., 1998, herein incorporated by reference).

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A variety of other agents may be included in the screening/identification assay. These include agents like salts, neutral proteins, e.g., albumin, detergents, etc. that are used to facilitate optimal protein—protein binding and/or reduce nonspecific or background interactions. Reagents that improve the efficiency of the assay, such as protease inhibitors, nuclease inhibitors, antimicrobial agents and the like may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 h will be sufficient.

The term "modulating the cell cycle progression" refers to altering the cell cycle by inhibiting its progress or by stimulating its progress. For example, inhibition of the cell cycle can be accomplished by inducing a gap phase that would not have occurred in the absence of modulation or increasing the duration of a gap phase relative to the duration in the absence of modulation. Stimulation of the cell cycle can be accomplished by eliminating a gap phase that would have occurred in the absence of modulation or decreasing the duration of a gap phase relative to the duration in the absence of modulation.

The term "reagent" as used herein describes any molecule, e.g., protein, nucleic acid, or pharmaceutical, with the capability of altering the expression of a Cds1 polynucleotide or activity of Cds1 polypeptide. Candidate reagents include nucleic acids encoding a Cds1 polypeptide, or that interfere with expression of a Cds1 polypeptide, such as an antisense nucleic acid, ribozymes, and the like. Candidate reagents further include antibodies that specifically recognize Cds1 polypeptides. Candidate reagents also encompass numerous chemical classes wherein the agent modulates Cds1 expression or activity. One exemplary reagent is a double stranded DNA molecule.

In yet another embodiment of the invention, there is provided a method of treating a disorder associated with cell cycle progression. The method includes administering to a subject in need thereof a therapeutically effective amount of a compound that modulates a Cds1 polypeptide activity.

In another embodiment of the invention, there is provided a method of treating a subject having a disorder associated with increased cell cycle progression compared to a subject not having the disorder. The method includes administering to a subject having the disorder a therapeutically effective amount of a compound that increases a Cds1 polypeptide activity.

Treatment of a disorder associated with cell cycle progression may influence phosphorylation of Cds1, activation of Cds1, phosphorylation of Cdc25, cell number, rounds of mitosis, DNA repair, functional properties of Cds1 proteins, and the like.

Modulation of a Cds1 polypeptide activity envisions the suppression of Cds1 activity or expression when Cds1 is overexpressed or has an increased activity as compared to a control. The term "modulate" also includes the augmentation of the expression of Cds1 polypeptide when it is underexpressed or has a decreased activity as compared to a control.

The disorder can be a cell proliferative disorder. A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is non-cancerous, e.g. its cells do not invade surrounding tissues or metastasize to distant sites. The term "malignant" refers to a tumor that is metastastic, invades contiguous tissue or no longer under normal cellular growth control. Neoplasms are generally derived from cells that normally maintain a proliferative capacity; almost every cell and tissue type can give rise to a neoplasm. For example, a mutation in the gene encoding CHK2, the human homologue of XCds1, appears to be involved in small cell lung cancer (Haruki et al. (2000) Cancer Research 60:4689–4692).

Where a disorder is associated with the increased expression of a Cds1 polypeptide, nucleic acid sequences that interfere with the expression of a Cds1 polypeptide can be used (see Kushner and Silverman (2000) Curr. Oncol. Reports, 2:23–30, herein incorporated by reference). In this manner, phosphorylation of a Cds1 or Cdc25 protein, cell cycle progression, and the like can be modulated. This approach also utilizes, for example, antisense nucleic acid, ribozymes, or triplex agents to block transcription or translation of a Cds1 mRNA, either by masking that mRNA with an antisense nucleic acid or triplex agent, or by cleaving it with a ribozyme in disorders associated with increased Cds1 expression. Alternatively, a dominant negative form of a Cds1 polypeptide could be administered.

When Cds1 is overexpressed, candidate agents include antisense nucleic acid sequences. Antisense nucleic acids are DNA or RNA molecules that are complementary to at least a portion of a specific mRNA molecule (Weintraub (1990) *Scientific American,* 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, (1988) *Anal. Biochem.,* 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al., (1991) *Antisense Res. and Dev.,* 1:227; Helene, (1991) *Anticancer Drug Design,* 6:569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, *J. Amer. Med. Assn.,* 260:3030). A major advantage of this approach is that, because they are sequence-specific, only mRNAs with particular sequences are inactivated.

There are two basic types of ribozymes namely, tetrahymena-type (Hasselhoff (1988) *Nature,* 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

When a disorder is associated with the decreased expression of a Cds1 polypeptide, nucleic acid sequences that encode a Cds1 polypeptide can be used. An agent which modulates Cds1 expression includes a polynucleotide encoding a polypeptide of SEQ ID NO:2, SEQ ID NO:4, or a conservative variant thereof. Alternatively, an agent of use with the subject invention includes reagents that increase the expression of a polynucleotide encoding Cds1 or a reagent that increases the activity of a Cds1 polypeptide.

The following examples are intended to illustrate but not limit the invention.

EXAMPLE 1

Isolation of a cDNA Encoding Xenopus Cds1 Homologue

To study the functional properties of Cds1 in Xenopus egg extracts, we isolated a cDNA encoding Xenopus Cds1 by using database analysis, polymerase chain reaction (PCR) amplification, and library screening.

An internal fragment of a cDNA encoding Xcds1 was obtained by polymerase chain reaction (PCR) using the degenerate oligonucleotides AA(T/C)GGIACIT(T/G)(T/C/G)ITIAA (SEQ ID NO:6) and ATIA(G/A)IAT(A/G)TTITCIGG(T/C)TTIAI(A/G)TCTC(T/G)(A/G)TG (SEQ ID NO:7), which were designed according to conserved areas found in Cds1 homologues. The PCR reactions contained Xenopus oocyte cDNAs as template, 50 pmol of the degenerate oligonucleotides, 200 µM of dNTPs, and 0.5 units of Taq polymerase in the buffer supplied by the manufacturer (GIBCO-BRL). PCR reactions were heated at 94° C. for 2 minutes followed by 30 cycles of amplification. Each cycle consisted of segments of 94° C. for 1 minute, 48° C. for 2 minutes, and 72° C. for 1 minute. An extra 10 minutes was added to the 72° C. extension step for the last cycle. The PCR products were separated on a 1% agarose gel. A 600-base pair DNA fragment was isolated from the gel and subsequently ligated to the vector pCR2.1 using the TA cloning kit (Stratagene). The 600-base pair insert was recovered from the vector by digesting with EcoRI and was then labeled with $^{32}$P. The probe ($3\times10^5$ cpm/µl) was denatured in boiling water for 5 minutes before being used to screen a Xenopus oocyte cDNA library (Mueller et al., (1995) Mol. Biol. Cell, 6:119–134). Approximately $1\times10^6$ independent colonies were screened. After secondary screening, a full-length cDNA clone was obtained. Both strands of the cDNA were sequenced by primer walking with a dye terminator cycle sequencing kit and an ABI model 373 automated sequencer (Perkin-Elmer Corp.).

The cDNA sequence contains a large open reading frame, a 3' poly(dA) stretch representing the poly(A) tail of the mRNA, and multiple in-frame translation termination codons upstream of the coding region.

Antibody Production.

To clone the coding sequence of Xcds1 into the expression vector pET30(a)+ (Novagen), a BamHI site upstream of the initiation codon and a XhoI site downstream of the termination codon were introduced by performing PCR with the primers GGACGTCGGATCCTCTCGTGATAC-TAAAACAGAG (SEQ ID NO:8) and GGACGTCCTC-GAGTTATCTTTTTGCTCTCTTTTCGG (SEQ ID NO:9). The resulting 1.5 kilobase PCR product was digested with BamHI and XhoI, and ligated to pET30(a)+ that had been digested with BamHI and XhoI. The pET30(a)-Xcds1 construct was introduced into the E. coli host strain BL21(DE3) pLysS (Novagen). Expression of His6-Xcds1 was induced by growing the cells at 37° C. for 3 hours in the presence of 0.4 mM IPTG. His6-Xcds1 was purified by nickel agarose chromatography, subjected to SDS-PAGE, and subsequently excised from the gel. Polyclonal rabbit antibodies against gel purified His6-Xcds1 were produced commercially (Covance Research Products Inc.). Antibodies against a peptide corresponding to the C-terminal end of Xcds1 (CSEILPTSAEKRAKR; SEQ ID NO: 10) were generated at another commercial facility (Zymed Laboratories Inc.).

The Xcds1 cDNA encodes a 58 kd translation product of 517 amino acids (FIG. 2). Xcds1 is most related to Chk2 (63% identical and 76% similar), the human homologue of Cds1 (Matsuoka et al., (1998) supra; Brown et al., (1999) supra; Blasina et al., (1999) supra; Chaturvedi et al., (1999) Oncogene, 18, 4047–4054). The most conserved areas are the carboxyl-terminal kinase domain and amino-terminal forkhead-associated domain (Matsuoka et al., 1998). The extreme amino-terminal region of Xcds1 is less conserved at the primary sequence level, but is rich in SQ and TQ amino acid pairs, which are part of the consensus site for phosphorylation by the DNA-dependent protein kinase family (Anderson, (1993) supra). By using histidine-tagged Xcds1 (His6-Xcds1) as antigen, polyclonal antibodies against Xcds1 were generated. Affinity-purified anti-Xcds1 antibodies recognized a single protein of approximately 58 kd in Xenopus egg extracts. Antibodies against the carboxyl-terminal 15 amino acids of Xcds1 recognized a polypeptide of the same size.

EXAMPLE 2

Preparation of Various DNA Templates and Egg Extracts

M13 single-stranded DNA was prepared according to a protocol included in a mutagenesis kit from Amersham (Oligonucleotide-directed in vitro mutagenesis system version 2). The pBS plasmids were prepared according to an alkaline lysis protocol (Sambrook et al., (1989) Mol. Cloning: a laboratory manual, Cold Spring Harbor Laboratory Press, Cold Spring Harbor, N.Y.). To generate linearized or open-circularized plasmids, ten microgram of plasmid pBS (Bluescript SK-phagemid, Stratagene) was either digested with restriction enzymes in the appropriate buffers under standard condition, or incubated at 56° C. for 36 hours in TE buffer (10 mM Tris HCl, 1 mM EDTA, pH 8.0). The resulting linearized and open-circularized plasmids were then diluted with distilled water to a concentration of 0.2 µg/µl. Untreated PBS was also diluted accordingly. Oligonucleotides were synthesized at the DNA Synthesis Facility of California Institute of Technology (Caltech). Concentrated oligonucleotides were diluted with distilled water to a concentration of 2 µg/µl. The sequences for the two complementary "random"-sequence oligonucleotides are GACTC-CGAGAACCAATTGC (Oligo 1; SEQ ID NO:3) and GCAATTGGTTCTCGGAGTC (Oligo 2; SEQ ID NO:4). The sequence for the oligonucleotide capable of forming a hairpin structure is GCGGCACGTTCTCGTGCCGC (Oligo 3; SEQ ID NO:5). Oligo 1 and Oligo 2 (10 µg each) were annealed in 20 µl of HBS buffer (10 mM HEPES, pH 7.5, 150 mM NaCl) in a water bath (500 ml of water) which was kept at 70° C. for 5 minutes and then cooled down at room temperature for 2.5 hrs. Oligo 3 (20 μg) was self-annealed by following the same procedure. To disrupt the duplex region, Oligo 3 was boiled in water for 10 minutes and then cooled on ice immediately.

Xenopus egg extracts were prepared as described (Murray, (1991) *Methods Cell Biol.* 36, 581–605) Extracts supplemented with 100 μg/ml of cycloheximide were incubated at 23° C. for 90 minutes following addition of DNA to a final concentration of either 10 ng/μl for plasmids and M13 DNA or 50 ng/μl for oligonucleotides.

EXAMPLE 3

Oligonucleotide Replication Assay

Oligonucleotides were labeled at the 5'-end with T4 polynucleotide kinase. Briefly, four microgram of each oligonucleotide was incubated with 100 μCi of $^{32}$P-ATP and 20 units of T4 polynucleotide kinase (New England Biolabs) in a total volume of 40 μl of reaction buffer (50 mM TrisCl, pH 7.5, 10 mM $MgCl_2$, 5 mM DTT). The reaction was performed at 37° C. for 45 minutes. At the end of the reaction, 60 μl of distilled water was added to the reaction followed by a spin-column purification (Sephadex G-50) to remove the unincorporated $^{32}$P-ATP. Ten microliter of the $^{32}$P-labeled oligonucleotides (approximately $1 \times 10^5$ cpm/μl) was added to 100 μl of interphase egg extract at room temperature. The first sample (10 μl of extract) was taken and frozen in liquid nitrogen immediately after addition of the oligonucleotides. An aliquot (10 μl) of extract was then taken and frozen every 15 minutes. All samples were thawed on ice and diluted 20-fold with HBS buffer (10 mM Hepes, 150 mM NaCl, pH 7.5). The diluted extract was deproteinized by extractions with an equal volume of phenol/chloroform (1:1) once and with chloroform three times. The protein-free sample (5 μl) was loaded onto a 10% native polyacrylamide gel for electrophoresis. The radiolabeled oligonucleotides were visualized by autoradiography.

EXAMPLE 4

Production of His6-Xcds1 and His6-Xcds1-N324A Proteins from Bacteria

To introduce the N324A mutation into the Xcds1 gene, two pairs of primers were used to amplify the wild-type Xcds1 sequence: GGACGTCGGATCCTCTCGTGATAC-TAAAACAGAG (SEQ ID NO:11) and GGACTGGGTC-GACGACAACAGCACAGCTTCAGGCTTCAG (SEQ ID NO:12); GGACGTCCTCGAGTTATCTTTTTGCTCTC TTTTCGG (SEQ ID NO:13) and GGTTGTCGTCGAC-TAGTGAAGAATGTTGCAT (SEQ ID NO:14). The resulting PCR products were digested with BamHI and SalI, and SalI and EcoRI, respectively, and ligated into the expression vector pET30(a)+ (Novagen) that had been digested with BamHI and EcoRI. A three-fragment ligation produced a construct pET30(a)-Xcds1-N324A. Both pET30(a)-Xcds1-N324A and pET30(a)-Xcds1 (constructed as described herein for antibody production) were introduced into the *E. coli* strain BL21(DE3)pLysS (Novagen). Expression of the His6-Xcds1 and His6-Xcds1-N324A proteins was induced by growing the cells at 30° C. for 3 hours in the presence of 0.4 mM IPTG in the medium. The proteins were purified using nickel agarose chromatography.

EXAMPLE 5

Kinase Assays

His6-Xcds1 or His6-Xcds1-N324A proteins were incubated with GST-Cdc25(254–316)-WT or GST-Cdc25 (254–316)-S287A in 20 μl of kinase buffer (10 mM Tris-HCl, pH 7.5, 10 mM $MgCl_2$, and 1 mM DTT) containing 2 μCi$^{32}$P-ATP and 10 μM ATP (Kumagai et al., (1998) *J. Cell Biol.*, 142, 1559–1569; herein incorporated by reference in its entirety). The reaction was performed at 23° C. for 15 minutes and terminated by adding 20 μl of gel loading buffer. The proteins were separated by SDS-PAGE and the phosphorylated proteins were detected using a PhosphorImager (Molecular Dynamics). To detect the kinase activity of endogenous Xcds1 protein, interphase egg extracts either lacking or containing poly(dT)$_{40}$ were incubated at 23° C. for 90 minutes. Next, the extracts were incubated with affinity-purified anti-Xcds1 antibodies bound to 10 μl of Affiprep protein A beads (Bio-Rad Laboratories) at 4° C. for 60 minutes. After centrifugation, the extract supernatant was removed. The Affiprep protein A beads were washed three times with 1 ml of 10 mM Hepes, pH 7.5, 150 mM NaCl, 30 mM glycerolphosphate, 0.1 mM $NaVO_4$, 0.5% NP-40, 0.1% SDS, 0.1 mM phenylmethylsulfonyl fluoride, 10 μg/ml of leupeptin, 10 μg/ml of chymostatin, and 10 μg/ml of pepstatin, and once with 1 ml of 10 mM Tris-HCl, pH 7.5, 10 mM $MgCl_2$, and 0.1 mM phenylmethylsulfonyl fluoride. Kinase reactions were performed at 23° C. for 15 minutes by incubating the immunoprecipitates in 20 μl of buffer containing 10 mM Tris-HCl, pH 7.5, 10 mM $MgCl_2$, 1 mM DTT, 2 μCi$^{32}$P-ATP, 10 μM ATP, and 2 μg of GST-Cdc25 (254–316)-WT.

EXAMPLE 6

Xcds1 is Phosphorylated in Response to Double-stranded DNA Ends

In fission yeast and human cells, Cds1 is phosphorylated and activated in response to DNA damage and/or replication blocks (Murakami and Okayama (1995) *Nature* 374, 817–819; Sanchez et al., (1996) *Science* 271, 357–360; Boddy et al., (1998) *Science* 280, 909–912; Lindsay et al., (1998). *Genes Dev.* 12, 382–395; Matsuoka et al., (1998) *Science* 282, 893–897; Brown et al., (1999) *Proc. Natl. Acad. Sci. USA* 96, 3745–3750; Blasina et al., (1999) *Curr. Biol.* 9, 1–10; Chaturvedi et al., (1999) *Oncogene* 18, 4047–4054; Brondello et al., (1999) *Mol. Cell. Biol.* 19, 4262–4269). To test whether Xcds1 is similarly modified, the endogenous Xcds1 protein in the nuclear fraction of Xenopus egg extracts was examined by immunoblotting.

Modifications of Xcds1 in response to M13 DNA and linearized plasmids were examined by immunoblot experiments. Interphase extracts containing 2,000 sperm nuclei/μl, 2,000 sperm nuclei/μl and 100 μl/ml aphidicolin, or 2,000 UV-damaged sperm nuclei/μl were incubated at 23° C. for 100 minutes. Seventy microliter of each extract was centrifuged through a sucrose cushion to isolate the nuclear fractions, which were subjected to SDS-PAGE and immunoblotting. After detection of Xcds1, the immunoblot was stripped and probed with anti-Xchk1 antibodies. Interphase egg extracts containing 10 ng/μl of M13 DNA or the same amount of M13 DNA and 5 μg/ml of actinomycin D were incubated at 23° C. An aliquot of extract (2 μl) was taken and frozen every 20 minutes after the addition of M13 DNA. Xcds1 protein in each aliquot was then detected by immunoblotting. Extracts containing various DNA templates (lanes 1–6) or the same DNA templates and 5 mM caffeine (lanes 7–12) were incubated at 23° C. for 90 minutes and then analyzed for Xcds1 protein by immunoblotting. The immunoblot was subsequently stripped and probed for Xchk1 protein.

Xcds1 did not show a reduction in mobility during SDS-polyacrylamide gel electrophoresis (SDS-PAGE) when chromosomal DNA replication was blocked by the DNA polymerase inhibitor aphidicolin or when the nuclear DNA was damaged with UV. In contrast, as was previously reported and confirmed herein, Xenopus Chk1 (Xchk1) was modified in response to both aphidicolin and UV (Kumagai et al., (1998) J. Cell Biol. 142, 1559–1569).

It has been reported that single-stranded M13 DNA also elicits a checkpoint response in Xenopus egg extracts (Kornbluth et al., (1992) Mol. Cell. Biol. 12, 3216–3223). While Xchk1 mediates the response to aphidicolin and UV (Kumagai et al., 1998, supra), it is unclear which effector kinase is regulated by M13 DNA. To examine this issue, single-stranded M13 DNA was added to interphase extracts at a concentration (10 ng/µl) that delays mitosis substantially (Kornbluth et al., 1992). Incubation of the extracts with M13 DNA for 40 minutes or longer resulted in a dramatic decrease in the electrophoretic mobility of Xcds1. This modification of Xcds1 was blocked by caffeine, an agent that overrides checkpoint. Conversely, M13 DNA did not trigger the modification of Xchk1.

Although M13 DNA was added to egg extracts in a single-stranded form, it is a very efficient template for DNA synthesis in such extracts. Within 40 minutes, it is quantitatively converted to double-stranded DNA, which mainly consists of three forms: closed-circular, open-circular, and linearized (Mechali and Harland, 1982). Significantly, the modification of Xcds1 did not occur until the M13 DNA had been incubated for 40–60 minutes in egg extracts, by which time the replication of this template has reached completion. Furthermore, inhibition of M13 DNA replication with actinomycin D (5 µg/ml) prevented the modification of Xcds1 (Mechali and Harland, (1982) Cell 30, 93–101). Therefore, it is possible that a form of double-stranded DNA derived from M13, but not the single-stranded DNA itself, is the checkpoint signal. To test this hypothesis, closed-circular plasmid DNA, plasmids linearized by restriction enzymes, or open-circular plasmids generated by heating at 56° C. were added separately to the extracts (Hofferer et al., (1995) Nuc. Acid. Res. 23, 1396–1397). Plasmids that had been digested with three different restriction enzymes, HindIII, SmaI, and KpnI, which respectively produce 3'-protruding, blunt, and 5'-protruding ends, strongly induced the modification of Xcds1. In contrast, closed-circular or open-circular plasmids did not have any effect. The modification of Xcds1 induced by linearized plasmids was also abolished by caffeine.

Unlike single-stranded DNA, double-stranded plasmid DNA is not efficiently replicated in whole egg extracts. Its metabolism in the extracts is not quite clear, except that it has been reported that linearized plasmids are partially re-circularized and multimerized by non-homologous end joining (Labhart, (1999) Mol. Cell. Biol. 19, 2585–2593). Nonetheless, the linearized plasmids appeared to mimic the presence of damaged DNA with double-stranded breaks, which induced the modification of Xcds1 in the extracts.

To evaluate further the nature of the checkpoint signal, other defined DNA molecules, i.e., four types of DNA homopolymers, each 40 nucleotides long, were added to the extracts. Extracts containing DNA homopolymers or the same DNA templates and 5 mM caffeine were incubated at 23° C. for 90 minutes and analyzed for Xcds1 protein by immunoblotting. The immunoblot was stripped and probed for Xchk1 protein. Radiolabeled poly(dT)$_{40}$, and poly(dC)$_{40}$, were incubated with 100 µl of interphase extract. Just after the addition of the homopolymers (marked as 0 min) and every 15 minutes (15–90 min) afterwards, a 10 µl sample was taken and deproteinized. The homopolymers were detected by autoradiography after native polyacrylamide gel electrophoresis. Interphase egg extracts containing 50 ng/µl of oligonucleotide duplex (oligo 1+oligo 2) were incubated at 23° C. An aliquot of extract (2 µl) was taken and frozen every 10 minutes after the addition of oligonucleotides. Xcds1 protein in each aliquot was detected by immunoblotting. Xcds1 protein immunoprecipitated from extracts containing 50 ng/µl of poly(dT)$_{40}$ was treated with either lambda phosphatase or buffer for 60 minutes or for 100 minutes at 30° C. As a control, Xcds1 was also immunoprecipitated from untreated interphase extracts. Xcds1 protein in the immunoprecipitates was examined by immunoblotting.

Interestingly, modification of Xcds1 occurred only in the extracts containing poly(dT)$_{40}$, and this modification was likewise sensitive to caffeine. Significantly, as is the case for M13 DNA, linearized plasmids and poly(dT)$_{40}$ did not induce the modification of Xchk1 under these conditions.

Why did poly(dT)$_{40}$ but not the homopolymers poly(dC)$_{40}$, poly(dA)$_{40}$, and poly(dG)$_{40}$ induce the modification of Xcds1? One plausible reason is that poly(dT)$_{40}$ could be converted to double-stranded DNA by replication in the egg extract, while the others remained as single-stranded oligonucleotides. Indeed, the eukaryotic DNA primase-polymerase a complex initiates RNA primer and DNA synthesis efficiently on polypyrimidinic templates in vitro (Gronostajski et al., (1984) J. Biol. Chem. 259, 9479–9484; Grosse and Krauss, (1985) J. Biol. Chem. 260, 1881–1888; Yamaguchi et al., (1985) J. Biol. Chem 260, 6254–6262; Yamaguchi et al., (1985) Mol. Cell. Biol. 5, 1170–1183), whereas primer synthesis on the polypurines poly(dG) and poly(dA) is negligible. Xenopus egg extracts contain a high concentration of ATP (>1 mM), which may both promote primer synthesis on poly(dT) and suppress formation of primers on poly(dC) (Yamaguchi et al., 1985, supra). One approach to test this hypothesis would be to examine the electrophoretic mobility of the homopolymers in a native polyacrylamide gel after incubation in egg extracts, since homopolymer duplexes usually migrate faster than the single-stranded ones. Experiments confirm that a poly(dT)$_{40}$:poly(dA)$_{40}$ duplex showed an increased mobility in a native gel compared to single-stranded poly(dT)$_{40}$. Poly(dT)$_{40}$ and the other homopolymers were labeled at the 5' end with $^{32}$P by using T4 polynucleotide kinase, and subsequently incubated in interphase egg extracts for 90 minutes. Most of poly(dT)$_{40}$, was converted within 15 minutes to a form that migrated faster in the gel at the position of a duplex. This conversion did not occur in the case of poly(dC)$_{40}$, poly(dG)$_{40}$, or poly(dA)$_{40}$. In agreement with these observations, it was found that an oligonucleotide duplex (19 base pairs) preformed from two complementary oligonucleotides with "random" sequences, and an oligonucleotide containing a hairpin structure both elicited the modification of Xcds1. In these experiments, double-stranded DNA ends were required for the modification of Xcds1, because each of the two "random"-sequence oligonucleotides by themselves did not have this effect, and because disruption of the hairpin structure by heating the oligonucleotide abolished its signaling capacity. The response of Xcds1 to the preformed oligonucleotide duplex occurred more quickly (within 20 minutes) than was the case for M13 DNA, which would be consistent with the notion that the duplex does not need to undergo replication to trigger a response from Xcds1.

Collectively, these findings strongly suggest that double-stranded DNA ends are the signal that triggers the modification of Xcds1. This modification represents phosphorylation because treatment of the modified Xcds1 with lambda phosphatase reversed the mobility alteration. Interestingly, the signaling from double-stranded DNA to Xcds1 is a process that does not require membranes or an intact nuclear environment, since the phosphorylation of Xcds1 in response to poly(dT)$_{40}$ occurred in membrane-free egg cytosol that was incubated under the same conditions as whole egg extracts.

EXAMPLE 7

Xcds1 is Activated by the Addition of Poly(dT)40 to Egg Extracts

It has been shown that fission yeast Cds1 and human Chk2/Cds1 phosphorylate Cdc25 within a 14-3-3 binding site (Zeng et al., (1998) Nature 395, 507–510; Matsuoka et al., (1998) supra; Brown et al., (1999) supra; Blasina et al., (1999) supra). The binding of 14-3-3 proteins to Cdc25 is required for a normal checkpoint response in humans, Xenopus egg extracts, and fission yeast (Peng et al., (1997) Science 277, 1501–1505; Kumagai etal., (1998), supra; Zeng etal., (1998)). Therefore, experiments were conducted to test whether Xcds1 would phosphorylate Xenopus Cdc25 in vitro.

His6-Xcds1 and His6-Xcds1-N324A were purified from E. coli and incubated with GST-Cdc25[254–316]-WT or GST-Cdc25[254–316]-S287A in kinase buffer containing $^{32}$P-ATP. The proteins were separated by SDS-PAGE and stained with Coomassie blue. The phosphorylated proteins were detected by using a PhosphorImager. Immunoprecipitation was performed from interphase egg cytosol containing poly(dT)$_{40}$ or no DNA using anti-Xcds1 antibodies or non-specific rabbit IgG. One third of each immunoprecipitate was analyzed for the modification of Xcds1 by immunoblotting; two thirds of each immunoprecipitate was incubated with GST-Cdc25[254–316]-WT to measure kinase activity.

His6-Xcds1, but not a catalytically inactive mutant (His6-Xcds1-N324A), phosphorylated a 62-amino acid region of Xenopus Cdc25 fused to glutathione S-transferase (GST-Cdc25[254–316]-WT) (Kumagai et al., (1998) supra). The phosphorylation occurs on Ser-287 in the 14-3-3 binding site of Xenopus Cdc25, because a serine-to-alanine mutation at this position abolished the phosphorylation. Similarly, endogenous Xcds1 immunoprecipitated from egg extracts phosphorylated this substrate well. Moreover, the hyperphosphorylated Xcds1 protein immunoprecipitated from extracts containing poly(dT)$_{40}$ showed a five- to six-fold increase over background in its kinase activity towards GST-Cdc25[254–316]-WT, indicating that this simple template also triggers the activation of Xcds1.

EXAMPLE 8

DNA Templates with Double-stranded DNA Ends Delay Mitosis

Single-stranded M13 DNA delays mitosis in cycling egg extracts, an effect that can be overridden by the base analogue caffeine (Kornbluth et al., (1992) supra). M13 DNA, as well as other simple DNA molecules that either contain or generate double-stranded ends, promote the phosphorylation of Xcds1. It is possible that M13 DNA delays mitosis by activating Xcds1. If this were the case, the other simple DNA molecules, such as poly(dT)$_{40}$, linearized plasmids, and oligonucleotide duplexes, might also delay mitosis because of their capacity to activate Xcds1.

The response of Xenopus egg extracts to poly(dT)$_{40}$ in the presence and absence of Xcds1 was assessed. Poly(dT)$_{40}$ or poly(dG)$_{40}$ was added to the extracts at a final concentration of 50 ng/µl in the presence or absence of 5 mM caffeine. The extracts were activated with CaCl$_2$ before the addition of DNA. Sperm nuclei (200 nuclei/µl) were added to the extracts in order to monitor the timing of nuclear envelope breakdown (NEB) by microscopy. The effect of removal of Xcds1 and Xchk1 proteins from egg extracts by immunodepletion was also examined. M-phase extract (100 µl) was incubated with a mixture of anti-Xcds1 antibodies (20 µg) and anti-Xchk1 antibodies (10 µg) bound to Affiprep protein A beads for 50 minutes at 4° C. with constant rocking. Protein A beads were removed by centrifugation. A second round of depletion was then performed to ensure that both Xcds1 and Xchk1 were completely removed, which was assessed by immunoblotting. As a control, M-phase extracts were treated by the same procedure with non-specific rabbit IgG. For depletion of Xcds1 alone, anti-Xchk1 antibodies were omitted. Depletion of Xcds1 does not diminish the mitotic delay caused by poly(dT)$_{40}$. Sperm nuclei (500 nuclei/µl) or both sperm nuclei (500 nuclei/µl) and poly(dT)$_{40}$ (50 ng/µl) were added to Xcds1-depleted or mock-depleted extracts.

Significantly, poly(dT)$_{40}$ was found to greatly delay mitosis in egg extracts as did M13 DNA and an oligonucleotide duplex. The delay of mitosis by poly(dT)$_{40}$ was partially but not completely reversed by caffeine. This observation is reminiscent of the fact that the aphidicolin-induced checkpoint in Xenopus egg extracts involves both caffeine-sensitive and caffeine-insensitive pathways (Kumagai et al., (1998), supra). In contrast, poly(dG)$_{40}$, which is not converted to a double-stranded form, did not significantly delay the timing of mitosis.

EXAMPLE 9

Immunodepletion of Xchk1 and Xcds1 From Egg Extracts Does Not Compromise the Mitotic Delay Induced by DNA Molecules with Double-stranded Ends To test whether Xcds1 mediates the mitotic delay induced by poly(dT)$_{40}$, Xcds1 was completely removed from egg extracts by immunodepletion.

One hundred microliter of M phase extract was incubated with either 20 µg of affinity-purified anti-Xcds1 antibodies, 10 µg of affinity-purified anti-Xchk1 antibodies, or both bound to 10 µl of Affiprep protein A beads (Bio-Rad Laboratories) at 4° C. for 50 minutes. The same amount of control rabbit IgG (Zymed Laboratories Inc.) was used for mock-depletion. After the incubation, the beads were removed by centrifugation. The supernatants were treated again under the same conditions to ensure that Xcds1 and/or Xchk1 were quantitatively removed from extracts.

The response of Xenopus egg extracts to an oligonucleotide duplex and M13 DNA in the presence and absence of Xcds1 was also examined. Sperm nuclei (500 nuclei/µl) or both sperm nuclei (500 nuclei/µl) and oligonucleotide duplex (oligo 1+oligo 2) (50 ng/µl) were added to Xcds1-depleted or mock-depleted extracts. Sperm nuclei (500 nuclei/µl) were also added to untreated extracts. The timing of nuclear envelope breakdown (NEB) was monitored by microscopy.

Interestingly, egg extracts lacking Xcds1 still displayed an intact mitotic delay in response to poly(dT)$_{40}$. Furthermore, depletion of Xcds1 did not compromise the delay of mitosis induced by M13 DNA or a double-stranded oligonucleotide. The fact that egg extracts containing double-stranded DNA ends arrest efficiently in the absence of Xcds1 could have several explanations. For example, it is possible that Xchk1 could compensate for the absence of Xcds1. Indeed, in fission yeast, Chk1 is mainly required for the damage checkpoint, but can substitute for Cds1 in the replication checkpoint when Cds1 is missing (Murakami and Okayama, (1995) supra; Lindsay et al., (1998) supra; Boddy et al., supra (1998); Brondello et al., (1999) supra). However, egg extracts lacking both Xcds1 and Xchk1 still underwent a mitotic delay in the presence of poly(dT)$_{40}$. Consistent with this observation, Xchk1 did not undergo checkpoint-associated phosphorylation in the presence of double-stranded DNA ends, even when Xcds1 had been removed.

EXAMPLE 10

Kinase Activity Towards Ser-287 Of Xcdc25 Remains In Egg Extracts Lacking Xcds1 and/or Xchk1

The assay for kinase activity toward Ser-287 of Xenopus Cdc25C in egg extracts was performed as described before (Kumagai et al., 1998, supra). To block chromosomal DNA replication, aphidicolin (dissolved in DMSO at 10 mg/ml) was added to egg extracts to a final concentration of 100 µg/ml.

Since Xchk1 does not undergo checkpoint-associated phosphorylation in the presence of double-stranded DNA ends even when Xcds1 has been removed, there could be a distinct checkpoint pathway(s) that acts independently of Xcds1 and Xchk1. This pathway could either be normally activated by the presence of double-stranded DNA ends or perhaps be activated when Xcds1 is absent. It seems plausible that vertebrates such as Xenopus could have checkpoint systems that are more complex than those of lower eukaryotes. To address this possibility, total kinase activity toward the substrate GST-Cdc25 [254–316]-WT was examined in egg extracts lacking Xchk1, Xcds1, or both.

M-phase extracts were immunodepleted with either anti-Xcds1 antibodies, anti-Xchk1 antibodies, both anti-Xcds1 and anti-Xchk1 antibodies, or non-specific rabbit IgG. The treated extracts were activated with CaCl2 and incubated at 23° C. for 90 minutes in the presence or absence of poly (dT)$_{40}$. Finally, total kinase activity towards GST-Cdc25 [254–316]-WT or GST-Cdc25[254–316]-S287A was assayed in each sample. Only kinase activity toward GST-Cdc25[254–316]-WT was quantitated, since phosphorylation of the S287A mutant was negligible.

Approximately 70% of the kinase activity toward Ser-287 of Cdc25 remained in egg extracts when both Xcds1 and Xchk1 were removed.

EXAMPLE 10

The biochemical properties of Xcds1, a Xenopus homologue of the checkpoint kinase Cds1 were analyzed. Collectively, these data make a strong case that templates containing double-stranded DNA ends trigger the phosphorylation of Xcds1. Nonetheless, the exact chemical nature of the DNA structure that is being recognized remains to be elucidated. Furthermore, poly(dT)$_{40}$, also elicited an increased kinase activity of Xcds1 toward Ser-287 in the 14-3-3 binding site of Xenopus Cdc25. Other templates are also likely to activate Xcds1. Since double-stranded DNA ends would typically be formed upon exposure to DNA damaging agents such as ionizing radiation, Xcds1 may normally be activated in response to this type of DNA damage in Xenopus cells.

Interestingly, the response of Xcds1 to DNA templates is quite distinct from that of Xchk1, a Xenopus homologue of Chk1. As described previously, Xchk1 undergoes a marked phosphorylation in egg extracts when replication is blocked by the DNA polymerase inhibitor aphidicolin or when UV-damaged sperm chromatin is added to the extracts (Kumagai et al., (1998) supra). In contrast, aphidicolin and UV damage do not elicit phosphorylation of Xcds1, as monitored by one-dimensional SDS-PAGE. Conversely, M13 DNA, linearized plasmids, double-stranded oligonucleotides, and poly(dT)$_{40}$, each of which caused a strong phosphorylation of Xcds1, did not have a detectable effect on Xchk1. It appears that Xcds1 and Xchk1 respond to quite different signals from DNA in the egg extract system. As shown herein, Xcds1 responds to double-stranded DNA ends, but the signal that leads to modification of Xchk1 is not known. In the presence of aphidicolin, the initial firing of replication origins can proceed but replication is blocked after the priming stage (Mahbubani et al., (1997) J. Cell. Biol. 136, 125–135), suggesting that some aspect of stalled DNA replication forks triggers the phosphorylation of Xchk1. UV radiation, which causes the formation of pyrimidine dimers, is also a very efficient signal for the modification of Xchk1. The recognition, excision, and/or repair of pyrimidine dimers by repair/replication factors in egg extracts could also lead to the modification of Xchk1. Furthermore, it is important to note that, at the doses of UV that were used, replication of UV-treated sperm chromatin in Xenopus egg extracts is strongly impaired. Thus, it is possible that aphidicolin and UV radiation both cause accumulation of a similar DNA structure, which may in turn lead to the modification of Xchk1.

Although Cds1 and Chk1 have been well conserved throughout evolution, the respective roles of these kinases in various checkpoint responses appear to vary depending on the species. In budding yeast, the closest homologue of Cds1 (Rad53) responds to both DNA damage (induced by exposure to methylmethane sulfonate) and DNA replication blocks (induced by treatment with hydroxyurea), although the response to hydroxyurea was less pronounced (Sun et al., (1996) Genes Dev. 10, 395–406; Sanchez etal., (1996) Science 277, 1497–1501. In wild-type fission yeast cells, Chk1 responds to DNA damage (induced by ionizing radiation, methylmethane sulfonate, or UV light), but not hydroxyurea treatment (Walworth and Bernards, (1996) Science 271, 353–356. However, in fission yeast mutants lacking Cds1, Chk1 does respond to hydroxyurea (Lindsay et al., (1998) supra; Boddy et al., (1998) supra; Brondello et al., (1999) supra. Although this finding may suggest that fission yeast Chk1 can also respond to DNA replication blocks, it has been proposed that Cds1 is required to suppress DNA damage in hydroxyurea-treated cells. Finally, fission yeast Cds1 responds strongly to treatment with hydroxyurea. Fission yeast Cds1 can also be activated in response to DNA damage, but its responsiveness to damage is restricted to S-phase (Murakami and Okayama, (1995) supra; Lindsay et al., (1998) supra; Brondello et al., (1999) supra). Collectively, the available data indicate that fission yeast Cds1 is activated by DNA replication blocks and exposure to damaging agents during S-phase, which may indirectly induce replication blocks. In contrast, Chk1 responds mainly to DNA damage and plays a more specialized role in the response to hydroxyurea. Thus, there appear to be significant differences between fission yeast and Xenopus egg extracts with respect to how Cds1 and Chk1 respond to the DNA structures that trigger checkpoints.

In human cells, Chk2, a Cds1 homologue, is activated upon exposure to ionizing radiation, UV light, and hydroxyurea, but the response to ionizing radiation is the strongest (Matsuoka et al., (1998) supra; Brown et al., (1999) supra. Significantly, the checkpoint kinase ATM, a member of the DNA-dependent protein kinase family that is defective in individuals with ataxia telangiectasia (AT), has been implicated as an upstream regulator of human Chk2/Cds1 (Matsuoka et al., (1998) supra; Brown et al., (1999) supra). AT cells are very sensitive to ionizing radiation, but display a normal DNA replication checkpoint (Cliby et al., (1998) EMBO J. 17, 159–168). Thus, although human Chk2/Cds1 appears to respond to a wider variety of signals than Xcds1, human Chk2/Cds1 is similar to Xcds1 in that it is clearly involved in a pathway that responds to ionizing radiation/double-stranded DNA breaks. Relatively less has been reported about the signals to which human Chk1 responds. Sanchez et al. ((1997) supra) found that that human Chk1 is modified in response to ionizing radiation, but the extent of modification was much less than what has been observed for human Chk2/Cds1 (Matsuoka et al., (1998) supra). The effect of hydroxyurea or other agents that induce DNA replication blocks on human Chk1 has not been reported. Accordingly, the role of human Chk1 in the DNA replication checkpoint is unclear at this time. Significantly, the Drosophila homologue of Chk1 (Grapes) has also been implicated in the replication checkpoint in fly embryos (Fogarty et al., (1997) Curr. Biol. 7, 418–426; Sibon et al., (1997) Nature 388, 93–97), suggesting that Xchk1 and at least one other metazoan Chk1 homologue may fulfill similar functions.

It was shown previously that the cell cycle delay in Xenopus egg extracts that is induced in response to treatment with aphidicolin involves multiple pathways: a caffeine-sensitive pathway containing Xchk1 and a caffeine-insensitive pathway. In view of the findings reported herein, Xcds1 is not a viable candidate for an effector of the caffeine-insensitive component of the aphidicolin-induced checkpoint for a number of reasons. First, Xcds1 is not phosphorylated in response to aphidicolin. Second, the phosphorylation of Xcds1 by the presence of double-stranded DNA ends in egg extracts is completely abolished by caffeine. Finally, immunodepletion of both Xcds1 and Xchk1 from egg extracts did not further compromise the aphidicolin-induced checkpoint in relation to extracts from which Xchk1 alone had been removed.

The pathways that control the response of egg extracts to double-stranded DNA ends may be even more complex than those that are triggered by DNA replication blocks. As is the case for aphidicolin, the delay of the cell cycle induced by poly(dT)$_{40}$ is only partially abrogated by treatment with caffeine. Thus, the cell cycle delay in response to poly(dT)$_{40}$ also appears to involve both caffeine-insensitive and caffeine-sensitive pathways. The nature of the caffeine-insensitive pathway(s) that is triggered by poly(dT)40 is unknown. Likewise, it is unclear whether aphidicolin and poly(dT)$_{40}$ trigger the same or distinct caffeine-insensitive pathways.

Since the phosphorylation/activation of Xcds1 in response to poly(dT)40 is abolished by caffeine, Xcds1 would be a candidate for a component of the caffeine-sensitive pathway(s). However, immunodepletion of Xcds1 does not compromise the cell cycle delay that is induced by poly(dT)$_{40}$. Similar results were obtained when M13 DNA or a double-stranded oligonucleotide were used to delay the cell cycle. It is possible that Xcds1 becomes phosphorylated due to the presence of various DNA templates, but does not play a role in the cell cycle delay that is triggered by them. This explanation would be somewhat unexpected in that Xcds1 does phosphorylate Xenopus Cdc25 well on Ser-287 in its 14-3-3 binding site. Cdc25 has been implicated as a target of the DNA replication/damage checkpoints in fission yeast, humans, and Xenopus egg extracts (Furnari et al., (1997) Science 277, 1495–1497; Sanchez et al., (1997) supra; Peng et al., (1997) supra; (Kumagai et al., (1998) supra), although an additional target(s) such as Wee1 could also be involved (O'Connell et al., (1997) EMBO J. 16, 545–554). On the other hand, Lindsay et al. ((1998) supra) have proposed that fission yeast Cds1 may play a distinct role in regulating the formation or stabilization of replication structures. If the function of Xcds1 does not involve delaying the cell cycle, the implication would be that there is another factor(s) in egg extracts that carries out this role in response to double-stranded DNA ends.

Another type of explanation for the intact checkpoint delay in Xcds1-depleted extracts is that another factor in these extracts acts redundantly with Xcds1. This putative factor would not appear to be Xchk1, because immunodepletion of Xchk1 alone or in combination with Xcds1 did not compromise the cell cycle delay in response to poly(dT)$_{40}$. However, approximately 70% of the total kinase activity towards Ser-287 of Cdc25 remains behind in egg extracts lacking both Xcds1 and Xchk1. It will be necessary to identify this Ser-287-specific kinase in order to evaluate the possibility that it contributes to cell cycle regulation in response to double-stranded DNA ends. The kinase(s) that lies upstream of Xcds1 in the pathways triggered by double-stranded DNA ends is currently unknown. In the human system, convincing evidence has been presented that ATM is an upstream regulator of human Chk2/Cds1 (Mutsuoka et al., (1998) supra; Brown et al., (1999) supra). AT cells are hypersensitive to ionizing radiation (Meyn, (1995) Cancer Res. 55, 5991–6061), which suggests that ATM is involved in mediating the response to double-stranded DNA ends. The recently described Xenopus homologue of ATM would be a good candidate for a regulator of Xcds1 (Robertson et al., (1999) Oncogene 18, 7070–7079). Since the agents to which Xchk1 responds are quite different from those which activate Xcds1, the implication is that ATM may not be the principal upstream regulator of Xchk1 in the replication checkpoint response.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polynucleotide encoding a substantially pure polypeptide as set forth in SEQ ID NO:2.

2. An isolated polynucleotide selected from:
   (a) a polynucleotide encoding a polypeptide as set forth in SEQ ID NO:2;
   (b) a polynucleotide of (a), wherein all T's are U
   (c) a polynucleotide complementary to the full length of (a) or (b); or
   (d) a polynucleotide as set forth in SEQ ID NO:1.

3. An isolated polynucleotide of claim 2 consisting of at least 15 continuous nucleotides that hybridize to a polynucleotide selected from the group consisting of:
   (a) a polynucleotide encoding a polypeptide consisting of amino acids 1 to 86 or amino acids 461 to 517 of SEQ ID NO:2;
   (b) a polynucleotide of (a), wherein T can be U;
   (c) a polynucleotide complementary to the full length of (a) or (b); or
   (d) a polynucleotide consisting of nucleotides 224 to 481 or nucleotides 1604 to 1770 of SEQ ID NO:1, wherein the hybridization and washing are in 0.2×SSC/0.1% SDS at about 42° C.

4. An expression vector comprising a polynucleotide of claim 2.

5. The expression vector of claim 4, wherein the vector is virus-derived.

6. The expression vector of claim 4, wherein the vector is plasmid-derived.

7. A host cell comprising a vector of claim 4.

8. A method for producing a polypeptide comprising the steps of:
   (a) culturing a host cell of claim 7 under conditions suitable for the expression of the polypeptide; and
   (b) recovering the polypeptide from the host cell culture.

* * * * *

SEQUENCE LISTING

<160> NUMBER OF SEQ ID NOS: 14

<210> SEQ ID NO 1
<211> LENGTH: 1845
<212> TYPE: DNA
<213> ORGANISM: Xenopus laevis

<400> SEQUENCE: 1

| | | | | | |
|---|---|---|---|---|---|
| ctgagatttt | acttgaaatg | aaggcgaggg | cctgataggt | tatgatttgc | aaagagcgtg | 60 |
| ggttcaggat | catttgtctg | tactgtaaag | tgttattagc | gctaatattt | cgcttcaggt | 120 |
| aaaagagggg | cgtgcgccac | agtgctgga | dacggggagc | gcctttccgc | tgctggagaa | 180 |
| acgcacgcac | attcacctgc | agcaaaacaa | gctttccagg | taaatgatgt | ctcgtgatac | 240 |
| taaaacagag | tcgcaacaat | ctcagggcac | ttcaagttcc | tcgtcctcca | gtgctcctca | 300 |
| atcttacagt | cagtcgtctt | catcgggtac | attaagttct | ttggatactg | ttccagtgca | 360 |
| agatcttgcg | tccattcctg | aagaccctga | gatagacgag | gatataccccc | agccttgggg | 420 |
| tcgtctctgg | gctcttggga | agggctttct | aaatcatgat | tgcctgcatg | aagaatatgt | 480 |
| atttggaaga | gacaaaaaat | gtgattacac | ctttgatatt | ccagtactaa | accagaccga | 540 |
| caggtacaaa | acatatagca | aaggcactt | cagaatattt | caggaattag | gtcatggaca | 600 |
| ctcccgtgtt | gctaacatag | aagatctgag | cggcaacgga | acatttgtta | caaggagat | 660 |
| tattggaaaa | gggcggacat | tgcctttaac | aaataatgcc | gagattgcac | tttcattacc | 720 |
| aactaataaa | gttttttgttt | tttcagattt | gtctgtggat | gatcagacta | tatatcctaa | 780 |
| ggacttcatt | gataaataca | tcatgtcaag | gccaatcgga | agtggggctt | gcggggaagt | 840 |
| gaaattggct | tttcaaaagt | cagtatgcaa | gaaggttgct | gtaaaaatca | tcagtaaaag | 900 |
| aaaatttaaa | atgaacactt | ctagtaatga | acacccctata | tctgttgaca | cagaaataga | 960 |
| gatcctgaaa | aaacttgatc | atccctgtat | cattaaaata | gagaattttt | ttgactctga | 1020 |
| ggacttctat | tacattgtgt | tggaactgat | ggaaggaggc | gaactgtttg | acagggtggt | 1080 |
| aaattcgaca | agactccgag | aaccaattgc | caaactgtat | ttttatcaga | tgctgctagc | 1140 |
| tgttcagtac | ctccatgaaa | atggggtgat | acatcgtgat | ctgaagcctg | aaaatgtgct | 1200 |
| gttgtcatcc | actagtgaag | aatgttgcat | aaagataacg | gattttggac | agtcaaaaat | 1260 |
| tctgggtgaa | acgtctttaa | tgagaacttt | gtgtggaact | cctacatact | tggcgcctga | 1320 |
| agttttgaat | acagcaggca | caactggata | cagtagtgca | gtggattgct | ggagtttagg | 1380 |
| agtcatcctt | tttgtgtgtc | tttgtggata | tccccccttt | tcagaacaaa | atagtaacat | 1440 |
| tcccttgaaa | aatcagattg | cagagggaaa | atacacctac | attgctgctg | cttggagaaa | 1500 |
| tgtatcagaa | caagcatttg | atttagtcaa | gaatcttctt | gttgttgatc | ctgagcaaag | 1560 |
| acttaccact | aaacaagcac | tggaacatcc | ctggcttcag | gacgattcta | tgaagcatac | 1620 |
| tgttgaaagg | ttaatgtatg | gggttgacca | cacaatgcct | cctccaatca | agaaaaacat | 1680 |
| aattcgaaaa | cggggacatg | aatgggatca | agatgccagt | acttcatctt | gctcagagat | 1740 |
| attaccaaca | tcagccgaaa | agagagcaaa | aagataaaac | aaaaaaaata | cattgcgctt | 1800 |
| tatttaataa | atgttttttgt | aaaaaaaaaa | aaaaaaaaaa | aaaaa | | 1845 |

<210> SEQ ID NO 2
<211> LENGTH: 517
<212> TYPE: PRT
<213> ORGANISM: Xenopus laevis

<400> SEQUENCE: 2

```
Met Met Ser Arg Asp Thr Lys Thr Glu Ser Gln Gln Ser Gln Gly Thr
1               5                   10                  15
Ser Ser Ser Ser Ser Ser Ala Pro Gln Ser Tyr Ser Gln Ser Ser
            20                  25                  30
Ser Ser Gly Thr Leu Ser Ser Leu Asp Thr Val Pro Val Gln Asp Leu
        35                  40                  45
Ala Ser Ile Pro Glu Asp Pro Glu Ile Asp Glu Asp Ile Pro Gln Pro
        50                  55                  60
Trp Gly Arg Leu Trp Ala Leu Gly Lys Gly Phe Leu Asn His Asp Cys
65                  70                  75                  80
Leu His Glu Glu Tyr Val Phe Gly Arg Asp Lys Lys Cys Asp Tyr Thr
                85                  90                  95
Phe Asp Ile Pro Val Leu Asn Gln Thr Asp Arg Tyr Lys Thr Tyr Ser
                100                 105                 110
Lys Arg His Phe Arg Ile Phe Gln Glu Leu Gly His Gly His Ser Arg
            115                 120                 125
Val Ala Asn Ile Glu Asp Leu Ser Gly Asn Gly Thr Phe Val Asn Lys
    130                 135                 140
Glu Ile Ile Gly Lys Gly Arg Thr Leu Pro Leu Thr Asn Asn Ala Glu
145                 150                 155                 160
Ile Ala Leu Ser Leu Pro Thr Asn Lys Val Phe Val Phe Ser Asp Leu
                165                 170                 175
Ser Val Asp Asp Gln Thr Ile Tyr Pro Lys Asp Phe Ile Asp Lys Tyr
                180                 185                 190
Ile Met Ser Arg Pro Ile Gly Ser Gly Ala Cys Gly Glu Val Lys Leu
            195                 200                 205
Ala Phe Gln Lys Ser Val Cys Lys Lys Val Ala Val Lys Ile Ile Ser
    210                 215                 220
Lys Arg Lys Phe Lys Met Asn Thr Ser Ser Asn Glu His Pro Ile Ser
225                 230                 235                 240
Val Asp Thr Glu Ile Glu Ile Leu Lys Lys Leu Asp His Pro Cys Ile
                245                 250                 255
Ile Lys Ile Glu Asn Phe Phe Asp Ser Glu Asp Phe Tyr Tyr Ile Val
                260                 265                 270
Leu Glu Leu Met Glu Gly Gly Glu Leu Phe Asp Arg Val Val Asn Ser
            275                 280                 285
Thr Arg Leu Arg Glu Pro Ile Ala Lys Leu Tyr Phe Tyr Gln Met Leu
    290                 295                 300
Leu Ala Val Gln Tyr Leu His Glu Asn Gly Val Ile His Arg Asp Leu
305                 310                 315                 320
Lys Pro Glu Asn Val Leu Leu Ser Ser Thr Ser Glu Glu Cys Cys Ile
                325                 330                 335
Lys Ile Thr Asp Phe Gly Gln Ser Lys Ile Leu Gly Glu Thr Ser Leu
                340                 345                 350
Met Arg Thr Leu Cys Gly Thr Pro Thr Tyr Leu Ala Pro Glu Val Leu
            355                 360                 365
Asn Thr Ala Gly Thr Thr Gly Tyr Ser Ser Ala Val Asp Cys Trp Ser
    370                 375                 380
Leu Gly Val Ile Leu Phe Val Cys Leu Cys Gly Tyr Pro Pro Phe Ser
385                 390                 395                 400
Glu Gln Asn Ser Asn Ile Pro Leu Lys Asn Gln Ile Ala Glu Gly Lys
```

```
                    405                 410                 415
Tyr Thr Tyr Ile Ala Ala Ala Trp Arg Asn Val Ser Glu Gln Ala Phe
                420                 425                 430

Asp Leu Val Lys Asn Leu Leu Val Val Asp Pro Glu Gln Arg Leu Thr
            435                 440                 445

Thr Lys Gln Ala Leu Glu His Pro Trp Leu Gln Asp Asp Ser Met Lys
        450                 455                 460

His Thr Val Glu Arg Leu Met Tyr Gly Val Asp His Thr Met Pro Pro
465                 470                 475                 480

Pro Ile Lys Lys Asn Ile Ile Arg Lys Arg Gly His Glu Trp Asp Gln
                485                 490                 495

Asp Ala Ser Thr Ser Ser Cys Ser Glu Ile Leu Pro Thr Ser Ala Glu
            500                 505                 510

Lys Arg Ala Lys Arg
        515

<210> SEQ ID NO 3
<211> LENGTH: 19
<212> TYPE: DNA
<213> ORGANISM: Artificial Sequence
<220> FEATURE:
<223> OTHER INFORMATION: Mitotic delay oligonucleotide

<400> SEQUENCE: 3
gactccgaga accaattgc                                                 19

<210> SEQ ID NO 4
<211> LENGTH: 19
<212> TYPE: DNA
<213> ORGANISM: Artificial Sequence
<220> FEATURE:
<223> OTHER INFORMATION: Mitotic delay oligonucleotide

<400> SEQUENCE: 4
gcaattggtt ctcggagtc                                                 19

<210> SEQ ID NO 5
<211> LENGTH: 20
<212> TYPE: DNA
<213> ORGANISM: Artificial Sequence
<220> FEATURE:
<223> OTHER INFORMATION: Mitotic delay oligonucleotide

<400> SEQUENCE: 5
gcggcacgtt ctcgtgccgc                                                20

<210> SEQ ID NO 6
<211> LENGTH: 17
<212> TYPE: DNA
<213> ORGANISM: Artificial Sequence
<220> FEATURE:
<223> OTHER INFORMATION: Degenerate oligonucleotide for PCR
<221> NAME/KEY: misc_feature
<222> LOCATION: (1)..(17)
<223> OTHER INFORMATION: n is Inosine

<400> SEQUENCE: 6
aayggnacnt kbntnaa                                                   17

<210> SEQ ID NO 7
<211> LENGTH: 32
<212> TYPE: DNA
<213> ORGANISM: Artificial Sequence
```

```
<220> FEATURE:
<223> OTHER INFORMATION: Degenerate oligonucleotide for PCR
<221> NAME/KEY: misc_feature
<222> LOCATION: (1)..(32)
<223> OTHER INFORMATION: n is Inosine

<400> SEQUENCE: 7
atnarnatrt tntcnggytt nanrtctckr tg                               32

<210> SEQ ID NO 8
<211> LENGTH: 34
<212> TYPE: DNA
<213> ORGANISM: Artificial Sequence
<220> FEATURE:
<223> OTHER INFORMATION: Primer for PCR

<400> SEQUENCE: 8
ggacgtcgga tcctctcgtg atactaaaac agag                             34

<210> SEQ ID NO 9
<211> LENGTH: 36
<212> TYPE: DNA
<213> ORGANISM: Artificial Sequence
<220> FEATURE:
<223> OTHER INFORMATION: Primer for PCR

<400> SEQUENCE: 9
ggacgtcctc gagttatctt tttgctctct tttcgg                           36

<210> SEQ ID NO 10
<211> LENGTH: 15
<212> TYPE: PRT
<213> ORGANISM: Artificial Sequence
<220> FEATURE:
<223> OTHER INFORMATION: C-terminal end of Xcds1

<400> SEQUENCE: 10

Cys Ser Glu Ile Leu Pro Thr Ser Ala Glu Lys Arg Ala Lys Arg
1               5                   10                  15

<210> SEQ ID NO 11
<211> LENGTH: 34
<212> TYPE: DNA
<213> ORGANISM: Artificial Sequence
<220> FEATURE:
<223> OTHER INFORMATION: Primer for PCR

<400> SEQUENCE: 11
ggacgtcgga tcctctcgtg atactaaaac agag                             34

<210> SEQ ID NO 12
<211> LENGTH: 39
<212> TYPE: DNA
<213> ORGANISM: Artificial Sequence
<220> FEATURE:
<223> OTHER INFORMATION: Primer for PCR

<400> SEQUENCE: 12
ggactgggtc gacgacaaca gcacagcttc aggcttcag                        39

<210> SEQ ID NO 13
<211> LENGTH: 36
<212> TYPE: DNA
<213> ORGANISM: Artificial Sequence
<220> FEATURE:
<223> OTHER INFORMATION: Primer for PCR
```

```
<400> SEQUENCE: 13
ggacgtcctc gagttatctt tttgctctct tttcgg                                  36

<210> SEQ ID NO 14
<211> LENGTH: 31
<212> TYPE: DNA
<213> ORGANISM: Artificial Sequence
<220> FEATURE:
<223> OTHER INFORMATION: Primer for PCR

<400> SEQUENCE: 14
ggttgtcgtc gactagtgaa gaatgttgca t                                       31
```